US008546083B2

(12) United States Patent
    Blaisdell

(10) Patent No.: US 8,546,083 B2
(45) Date of Patent: Oct. 1, 2013

(54) MOLECULAR ACCESSIBILITY ASSAY

(75) Inventor: Jeffrey O. Blaisdell, Colchester, VT (US)

(73) Assignees: University of Vermont, Burlington, VT (US); The University of Vermont and State Agricultural College, Burlington, VT (US)

( * ) Notice: Subject to any disclaimer, the term of this patent is extended or adjusted under 35 U.S.C. 154(b) by 622 days.

(21) Appl. No.: 12/449,042

(22) PCT Filed: Jan. 18, 2008

(86) PCT No.: PCT/US2008/000664
    § 371 (c)(1),
    (2), (4) Date: Nov. 6, 2009

(87) PCT Pub. No.: WO2008/091541
    PCT Pub. Date: Jul. 31, 2008

(65) Prior Publication Data
    US 2010/0047791 A1    Feb. 25, 2010

Related U.S. Application Data

(60) Provisional application No. 60/881,614, filed on Jan. 22, 2007.

(51) Int. Cl.
    *C12Q 1/68*    (2006.01)
    *C07K 14/00*   (2006.01)
(52) U.S. Cl.
    USPC .......................................... 435/6.12; 530/350
(58) Field of Classification Search
    None
    See application file for complete search history.

(56) References Cited

U.S. PATENT DOCUMENTS

| 5,800,989 | A  | * | 9/1998  | Linn et al.     | 435/6.11 |
| 6,951,726 | B2 | * | 10/2005 | Bilodeau et al. | 435/6.16 |
| 2002/0061531 | A1 | * | 5/2002 | Le           | 435/6 |

OTHER PUBLICATIONS

Albert et al., Heterogeneity in the actions of drugs that bind in the DNA minor groove. Biochemistry. Aug. 3, 1999;38(31):10135-46.
Back et al., A distinct TthMutY bifunctional glycosylase that hydrolyzes not only adenine but also thymine opposite 8-oxoguanine in the hyperthermophilic bacterium, *Thermus thermophilus*. DNA Repair (Amst). Aug. 13, 2006;5(8):894-903. Epub Jun. 14, 2006.
Bandaru et al., A novel human DNA glycosylase that removes oxidative DNA damage and is homologous to *Escherichia coli* endonuclease VIII. DNA Repair (Amst). Jul. 17, 2002;1(7):517-29.
Bandaru et al., Oxidative DNA glycosylases: recipes from cloning to characterization. Methods Enzymol. 2006;408:15-33.
Berti et al., Toward a detailed understanding of base excision repair enzymes: transition state and mechanistic analyses of N-glycoside hydrolysis and N-glycoside transfer. Chem Rev. Feb. 2006;106(2):506-55.

Blaisdell et al., Rapid determination of the active fraction of DNA repair glycosylases: a novel fluorescence assay for trapped intermediates. Nucleic Acids Res. 2007;35(5):1601-11. Epub Feb. 8, 2007.
Burgess et al., Determination of active site residues in *Escherichia coli* endonuclease VIII. J Biol Chem. Jan. 25, 2002;277(4):2938-44. Epub Nov. 15, 2001.
Chuprina et al., Molecular dynamics simulation of the hydration shell of a B-DNA decamer reveals two main types of minor-groove hydration depending on groove width. Proc Natl Acad Sci U S A. Jan. 15, 1991;88(2):593-7.
Dany et al., A functional OGG1 homologue from *Arabidopsis thaliana*. Mol Genet Genomics. Apr. 2001;265(2):293-301.
Demott et al., Covalent trapping of human DNA polymerase beta by the oxidative DNA lesion 2-deoxyribonolactone. J Biol Chem. Mar. 8, 2002;277(10):7637-40. Epub Jan. 22, 2002.
Doi et al., Synthesis and characterization of oligonucleotides containing 2'-fluorinated thymidine glycol as inhibitors of the endonuclease III reaction. Nucleic Acids Res. Mar. 17, 2006;34(5)1540-51.
Eggleston et al., A helicase assay based on the displacement of fluorescent, nucleic acid-binding ligands. Nucleic Acids Res. Apr. 1, 1996;24(7):1179-86.
Eriksson et al., Binding of 4',6-diamidino-2-phenylindole (DAPI) to AT regions of DNA: evidence for an allosteric conformational change. Biochemistry. Mar. 30, 1993;32(12):2987-98.
Fromme et al., Structure of a trapped endonuclease III-DNA covalent intermediate. EMBO J. Jul. 1, 2003;22(13):3461-71.
Ghosh et al., C-H.O hydrogen bonds in minor groove of A-tracts in DNA double helices. J Mol Biol. Dec. 17, 1999;294(5):1149-58.
Gilboa et al., Structure of formamidopyrimidine-DNA glycosylase covalently complexed to DNA. J Biol Chem. May 31, 2002;277(22):19811-6. Epub Mar. 23, 2002.
Hashimoto et al., The 2-deoxyribonolactone lesion produced in DNA by neocarzinostatin and other damaging agents forms cross-links with the base-excision repair enzyme endonuclease III. J Am Chem Soc. Apr. 4, 2001;123(13):3161-2.
Holub et al., "Second order" sequence specificity of DAPI-binding to at-regions in DNA. 43rd Annual Meeting Biophysical Society. Biophys J (Annual Meeting Abstracts). 1999;76:A129.
Huffman et al., DNA base damage recognition and removal: new twists and grooves. Mutat Res. Sep. 4, 2005;577(1-2):55-76.
Ide et al., Human DNA glycosylases involved in the repair of oxidatively damaged DNA. Biol Pharm Bull. Apr. 2004;27(4):480-5. Review.
Ikeda et al., Purification and characterization of human NTH1, a homolog of *Escherichia coli* endonuclease III. Direct identification of Lys-212 as the active nucleophilic residue. J Biol Chem. Aug. 21, 1998;273(34):21585-93.
Im et al., Functional identification of an 8-oxoguanine specific endonuclease from *Thermotoga maritima*. J Biochem Mol Biol. Nov. 30, 2005;38(6):676-82.
Kapuściński et al., Fluorescent complexes of DNA with DAPI 4',6-diamidine-2-phenyl indole.2HCI or DCI 4',6-dicarboxyamide-2-phenyl indole. Nucleic Acids Res. Oct. 1978;5(10):3775-99.
Larsen et al., The structure of DAPI bound to DNA. J Biomol Struct Dyn. Dec. 1989;7(3):477-91.
Lu et al., Characterization of an *Escherichia coli* mutant MutY with a cysteine to alanine mutation at the iron-sulfur cluster domain. Biochemistry. Apr. 8, 2003;42(13):3742-50.

(Continued)

*Primary Examiner* — Prabha Chunduru
(74) *Attorney, Agent, or Firm* — Wolf, Greenfield & Sacks, P.C.

(57) ABSTRACT

Methods and compositions are provided for determining polypeptide-nucleic acid interactions.

15 Claims, 8 Drawing Sheets

(56) References Cited

OTHER PUBLICATIONS

Manuel et al., Reaction intermediates in the catalytic mechanism of *Escherichia coli* MutY DNA glycosylase. J Biol Chem. Nov. 5, 2004;279(45):46930-9. Epub Aug. 23, 2004.

Manzini et al., Interaction of diamidino-2-phenylindole (DAPI) with natural and synthetic nucleic acids. Nucleic Acids Res. Dec. 20, 1983;11(24):8861-76.

Marenstein et al., Stimulation of human endonuclease III by Y box-binding protein 1 (DNA-binding protein B). Interaction between a base excision repair enzyme and a transcription factor. J Biol Chem. Jun. 15, 2001;276(24):21242-9. Epub Apr. 3, 2001.

Matsubara et al., Mammalian 5-formyluracil-DNA glycosylase. 1. Identification and characterization of a novel activity that releases 5-formyluracil from DNA. Biochemistry. May 6, 2003;42(17):4993-5002.

Mohan et al., A study of the interaction of DAPI with DNA containing AT and non-AT sequences—molecular specificity of minor groove binding drugs. J Biomol Struct Dyn. Feb. 1994;11(4):849-67.

Nakano et al., DNA-protein cross-link formation mediated by oxanine. A novel genotoxic mechanism of nitric oxide-induced DNA damage. J Biol Chem. Jul. 4, 2003;278(27):25264-72. Epub Apr. 27, 2003.

Neidle, Minor-groove width and accessibility in B-DNA drug and protein complexes. FEBS Lett. Feb. 17, 1992;298(1):97-9.

Porello et al., Single-turnover and pre-steady-state kinetics of the reaction of the adenine glycosylase MutY with mismatch-containing DNA substrates. Biochemistry. Oct. 20, 1998;37(42):14756-64.

Rieger et al., Characterization of a cross-linked DNA-endonuclease VIII repair complex by electrospray ionization mass spectrometry. J Am Soc Mass Spectrom. Jun. 2000;11(6):505-15.

Saparbaev et al., Repair of oxidized purines and damaged pyrimidines by *E. coli* Fpg protein: different roles of proline 2 and lysine 57 residues. Environ Mol Mutagen. 2002;39(1):10-7.

Sidorkina et al., Role of the N-terminal proline residue in the catalytic activities of the *Escherichia coli* Fpg protein. J Biol Chem. Apr. 7, 2000;275(14):9924-9.

Spacková et al., Molecular dynamics simulations and thermodynamics analysis of DNA-drug complexes. Minor groove binding between 4',6-diamidino-2-phenylindole and DNA duplexes in solution. J Am Chem Soc. Feb. 19, 2003;125(7):1759-69.

Stivers et al., A mechanistic perspective on the chemistry of DNA repair glycosylases. Chem Rev. Jul. 2003;103(7):2729-59.

Travers, DNA conformation and protein binding. Annu Rev Biochem. 1989;58:427-52.

Trotta et al., 1H NMR study of [d(GCGATCGC)]2 and its interaction with minor groove binding 4',6-diamidino-2-phenylindole. J Biol Chem. Feb. 25, 1993;268(6):3944-51.

Van Hecke et al., Netropsin interactions in the minor groove of d(GGCCAATTGG) studied by a combination of resolution enhancement and ab initio calculations. FEBS J. Jul. 2005;272(14):3531-41.

Verdine et al., Covalent trapping of protein-DNA complexes. Annu Rev Biochem. 2003;72:337-66. Review.

Vlieghe et al., Crystal structure of d(GGCCAATTGG) complexed with DAPI reveals novel binding mode. Biochemistry. Dec. 14, 1999;38(50):16443-51.

Wallace et al., Biological consequences of free radical-damaged DNA bases. Free Radic Biol Med. Jul. 1, 2002;33(1):1-14.

Williams et al., Evidence that MutY is a monofunctional glycosylase capable of forming a covalent Schiff base intermediate with substrate DNA. Nucleic Acids Res. Nov. 15, 1998;26(22):5123-33.

Williams et al., Formation of a Schiff base intermediate is not required for the adenine glycosylase activity of *Escherichia coli* MutY. Biochemistry. Nov. 23, 1999;38(47):15417-24.

Wilson et al., DNA sequence dependent binding modes of 4',6-diamidino-2-phenylindole (DAPI). Biochemistry. Sep. 11, 1990;29(36):8452-61.

Zaitsev et al., Binding of double-stranded DNA by *Escherichia coli* RecA protein monitored by a fluorescent dye displacement assay. Nucleic Acids Res. Jan. 15, 1998;26(2):650-4.

Zharkov et al., NH2-terminal proline acts as a nucleophile in the glycosylase/AP-lyase reaction catalyzed by *Escherichia coli* formamidopyrimidine-DNA glycosylase (Fpg) protein. J Biol Chem. Feb. 21, 1997;272(8):5335-41.

Zharkov et al., Role for lysine 142 in the excision of adenine from A:G mispairs by MutY DNA glycosylase of *Escherichia coli*. Biochemistry. Dec. 5, 2000;39(48):14768-78.

Zharkov et al., Substrate specificity and reaction mechanism of murine 8-oxoguanine-DNA glycosylase. J Biol Chem. Sep. 15, 2000;275(37):28607-17.

* cited by examiner

MOLECULAR ACCESSIBILITY ASSAY

RELATED APPLICATIONS

This application is a national stage filing under U.S.C. §371 of PCT International application PCT/US2008/000664, filed Jan. 18, 2008, which was published under PCT Article 21(2) in English, and claims the benefit under 35 U.S.C. §119(e) of U.S. provisional application Ser. No. 60/881,614, filed Jan. 22, 2007, the disclosure of each referenced application is incorporated by reference herein in its entirety.

GOVERNMENT SUPPORT

This invention is at least in part the result of work that was supported by the National Institutes of Health Grant (P01 CA098993) awarded by the National Cancer Institute. The government has certain rights in this invention.

FIELD OF THE INVENTION

This invention relates, in part, to assays and kits for determining polypeptide-nucleic acid interactions.

BACKGROUND

Current methods to measure the fraction of active glycosylase molecules in a given enzyme preparation are slow and cumbersome. A commonality among these and other techniques to assess levels and activity of DNA binding polypeptides is the almost universal requirement for separation of the trapped complex from unbound DNA via polyacrylamide gel electrophoresis (PAGE) prior to imaging analysis (e.g., PhosphorImager analysis). A faster, less cumbersome, and more efficient technique would be useful for the detection and quantification of DNA binding polypeptides.

SUMMARY OF THE INVENTION

The invention relates, in part, to assays and methods for assessing the amount of bound nucleic acid-binding polypeptides in samples. The determination of the amount of bound nucleic acid-binding polypeptide in a sample can be used to determine characteristics of the nucleic acid-binding polypeptide, the sample, the source from which the sample was obtained, the rate of reaction between the binding polypeptide and nucleic acid, the type of reaction between the binding polypeptide and the nucleic acid, etc. nucleic acids to which they bind, etc. Assays and kits of the invention provide information about the binding of nucleic acid binding polypeptides and the nucleic acid molecules to which they bind.

According to one aspect of the invention, methods for assaying the amount of bound nucleic acid-binding polypeptide in a sample are provided. The methods include the step of: (a) measuring the level of fluorescence in a sample comprising a nucleic acid, a nucleic acid binding fluorescent reporter, and a nucleic acid-binding polypeptide, wherein the nucleic acid sequence comprises a fluorescent reporter binding sequence and a binding polypeptide binding sequence positioned such that binding polypeptide bound to the nucleic acid inhibits binding of the fluorescent reporter to the nucleic acid and modulates the level of fluorescence in the sample, and (b) comparing the level of fluorescence in the sample to a control level of fluorescence, wherein a difference in the level of fluorescence in the sample compared to the control level of fluorescence indicates the amount of bound nucleic acid-binding polypeptide in the sample. In some embodiments, the amount of bound nucleic acid is higher in the sample than in the control and in some embodiments, the amount of bound nucleic acid is lower than in the control. In some embodiments, the nucleic acid-binding polypeptide is a DNA-binding polypeptide. In certain embodiments, the DNA-binding polypeptide is an enzyme, histone, telomere binding polypeptide, transcription factor, or other regulatory polypeptide. In some embodiments, the enzyme is a glycosylase, polymerase, nuclease, methyl transferase, or topoisomerase. In some embodiments, the sample is obtained from an enzyme preparation or cell extract. In certain embodiments, the fluorescent reporter is a fluorescent molecule whose fluorescence is modified when the reporter binds a nucleic acid compared to the fluorescence of the reporter when not bound to the nucleic acid. In some embodiments, the fluorescent reporter is fluorescent 4',6-diamidino-2-phenylindole (DAPI), distamycin A, Hoechst 33258, netropsin, berenil, 2-hydroxystilbamidine, chromomycin A3, or a fluorophore-tethered nucleic acid or oligopeptide. In some embodiments, the nucleic acid has a sequence comprising two or more fluorescent reporter-binding sequences and/or two or more binding polypeptide binding sequences positioned such that binding polypeptide bound to the nucleic acid interferes with binding of the fluorescent reporter to the nucleic acid. In certain embodiments, the nucleic acid is a natural, synthetic, or modified DNA or RNA. In some embodiments, the binding polypeptide binding sequence of the nucleic acid is a telomere, undamaged nucleic acid subsequence, one or more methylated nucleic acid bases, or one or more damaged nucleic acid bases. In some embodiments, the damaged nucleic acid base comprises at least one 5,6-dihydrouracil, 7,8-dihydro-8-oxoguanine, 5,6-dihydroxy-5,6-dihydrothymine, 5-hydroxycytosine, 5,6-dihydrothymine, 5-hydroxyuracil, or 7,8-dihydro-8-oxoadenine. In some embodiments, the binding polypeptide is covalently or non-covalently bound to the nucleic acid. In certain embodiments, the binding polypeptide is covalently bound to the nucleic acid by an intermediate trapped by a trapping agent. In some embodiments, the intermediate is a Schiff base. In some embodiments, the trapping agent is 2-deoxyribonolactone, oxanine, or, cis-Platinum. In certain embodiments, the trapping agent is a reducing agent. In some embodiments, the reducing agent is a borohydride compound, $NaBH_4$ or $NaCNBH_3$. In some embodiments, the method is carried out in a microplate format. In some embodiments, the unbound nucleic acid is not detectably labeled.

According to another aspect of the invention, compositions are provided. The compositions include a nucleic acid comprising a fluorescent reporter binding sequence and a binding polypeptide binding sequence positioned such that a binding polypeptide bound to the nucleic acid inhibits binding of the fluorescent reporter to the nucleic acid. In certain embodiments, the nucleic acid-binding polypeptide is a DNA-binding polypeptide. In some embodiments, the DNA-binding polypeptide is an enzyme, histone, telomere binding polypeptide, transcription factor, or other regulatory polypeptide. In some embodiments, the enzyme is a glycosylase, polymerase, nuclease, methyl transferase, or topoicertainrase. In some embodiments, the fluorescent reporter is a fluorescent molecule whose fluorescence is modified when the reporter binds a nucleic acid compared to the fluorescence of the reporter when not bound to the nucleic acid. In some embodiments, the fluorescent reporter is fluorescent 4',6-diamidino-2-phenylindole (DAPI), distamycin A, Hoechst 33258, netropsin, berenil, 2-hydroxystilbamidine, chromomycin A3, or a fluorophore-tethered nucleic acid or oligopeptide. In certain embodiments, the nucleic acid has a sequence comprising two or more fluorescent reporter-binding sequences and/or two or more binding polypeptide binding sequences positioned such that binding polypeptide bound to the nucleic acid interferes with binding of the fluorescent reporter to the nucleic acid. In some embodiments, the nucleic acid is a natural, synthetic, or modified DNA or RNA. In some embodiments, the binding polypeptide binding sequence of the nucleic acid is a telomere, undamaged nucleic acid subsequence, one or more methylated nucleic acid bases, or one or more damaged nucleic acid bases. In certain embodiments, the damaged nucleic acid base comprises at least one 5,6-dihydrouracil, 7,8-dihydro-8-oxoguanine, 5,6-dihydroxy-5,6-dihydrothymine, 5-hydroxycytosine, 5,6-dihydrothymine, 5-hydroxyuracil, or 7,8-dihydro-8-oxoadenine. In some embodiments, the binding polypeptide is covalently or non-covalently bound to the nucleic acid. In some embodiments, the binding polypeptide is covalently bound to the nucleic acid by an intermediate trapped by a trapping agent. In certain embodiments, the intermediate is a Schiff base. In some embodiments, the trapping agent is 2-deoxyribonolactone, oxanine, or cis-Platinum. In some embodiments, the trapping agent is a reducing agent. In some embodiments, the reducing agent is a borohydride compound, $NaBH_4$ or $NaCNBH_3$. In certain embodiments, the unbound nucleic acid is not detectably labeled.

According to yet another aspect of the invention, kits are provided. Kits of the invention may include a container containing any of the aforementioned compositions, and instructions for use of the composition to assay activity of a nucleic acid binding polypeptide in a sample.

According to yet another aspect of the invention, methods for identifying whether a candidate agent modulates binding of a nucleic acid binding polypeptide to a nucleic acid are provided. The methods include contacting the candidate agent with a sample comprising a nucleic acid, a nucleic acid binding fluorescent reporter, and a nucleic acid-binding polypeptide, wherein the nucleic acid sequence comprises a fluorescent reporter binding sequence and a binding polypeptide binding sequence positioned such that binding polypeptide bound to the nucleic acid interferes with binding of the fluorescent reporter to the nucleic acid and modulates the level of fluorescence in the sample, measuring the amount of fluorescence in the sample, and comparing the level of fluorescence in the sample to a control level of fluorescence in a control sample not contacted with the agent, wherein a difference in the level of fluorescence in the sample compared to the control level of fluorescence identifies the agent as modulating the binding of the nucleic acid-binding polypeptide in the sample. In some embodiments, the amount of fluorescence is higher in the sample than in the control sample and in some embodiments, the amount of fluorescence is lower in the sample than in the control sample. In certain embodiments, the nucleic acid-binding polypeptide is a DNA-binding polypeptide. In some embodiments, the DNA-binding polypeptide is an enzyme, histone, telomere binding polypeptide, transcription factor, or other regulatory polypeptide. In some embodiments, the enzyme is a glycosylase, polymerase, nuclease, methyl transferase, or topoicertainrase. In some embodiments, the sample is obtained from an enzyme preparation or cell extract. In some embodiments, the fluorescent reporter is a fluorescent molecule whose fluorescence is modified when the reporter binds a nucleic acid compared to the fluorescence of the reporter when not bound to the nucleic acid. In certain embodiments, the fluorescent reporter is fluorescent 4',6-diamidino-2-phenylindole (DAPI), distamycin A, Hoechst 33258, netropsin, berenil, 2-hydroxystilbamidine, chromomycin A3, or a fluorophore-tethered nucleic acid or oligopeptide. In some embodiments, the nucleic acid has a sequence comprising two or more fluorescent reporter-binding sequences and/or two or more binding polypeptide binding sequences positioned such that binding polypeptide bound to the nucleic acid interferes with binding of the fluorescent reporter to the nucleic acid. In some embodiments, the nucleic acid is a natural, synthetic, or modified DNA or RNA. In some embodiments, the binding polypeptide binding sequence of the nucleic acid is a telomere, undamaged nucleic acid subsequence, one or more methylated nucleic acid bases, or one or more damaged nucleic acid bases. In certain embodiments, the damaged nucleic acid base comprises at least one 5,6-dihydrouracil, 7,8-dihydro-8-oxoguanine, 5,6-dihydroxy-5,6-dihydrothymine, 5-hydroxycytosine, 5,6-dihydrothymine, 5-hydroxyuracil, or 7,8-dihydro-8-oxoadenine. In some embodiments, the binding polypeptide is covalently or non-covalently bound to the nucleic acid. In some embodiments, the binding polypeptide is covalently bound to the nucleic acid by an intermediate trapped by a trapping agent. In certain embodiments, the intermediate is a Schiff base. In some embodiments, the trapping agent is 2-deoxyribonolactone, oxanine, or, cis-Platinum. In some embodiments, the trapping agent is a reducing agent. In some embodiments, the reducing agent is a borohydride compound, $NaBH_4$ or $NaCNBH_3$. In certain embodiments, the method is carried out in a microplate format. In some embodiments, the unbound nucleic acid is not detectably labeled.

BRIEF DESCRIPTION OF THE DRAWINGS

FIG. 1A shows the quantity of ES complex formed in a standard gel-based Schiff base assay as related to the total enzyme concentration, $E_T$, plotted by the equation $ES=\min(\alpha E_T, \beta S_T)$, where $\alpha$ is the active enzyme fraction, $\beta$ the fraction of cleavable substrate, and $S_T$ the total substrate added. FIG. 1B shows a dashed line representing the quantity of ES* complex formed in the DAPI molecular accessibility assay as related to the total enzyme concentration, $E_T$, plotted by the equation $ES=\min(\alpha E_T \Phi_1, \beta S_T \Phi_2)$, where $\alpha$, $\beta$, and $S_T$ are as above, $0 \leq \Phi_{1,2} \leq 1$ is the accessibility parameter, and $ES^* \leq ES$.

FIGS. 2A and 2D show a gel-shift and ES concentration plot wherein 0, 50, 100, 200, 400, and 800 nM EcoNth was incubated for 30 minutes at 37° C. with 100 nM of 35DHU substrate in the presence of 50 mM sodium borohydride. FIGS. 2B-F show ES concentration plots wherein 0, 50, 100, 200, 400, and 800 nM EcoNth was incubated for 30 minutes at 37° C. with 100 nM of 4L, 5L, 5R, or N5R substrates in the presence of 50 mM sodium borohydride. FIGS. 2G and 2J show a gel-shift and ES concentration plot wherein 0, 50, 100, 200, 400, and 800 nM EcoNth was incubated for 30 minutes at 37° C. with 100 nM of 35DHU substrate in the presence of 50 mM sodium cyanoborohydride. FIGS. 2H-L show ES concentration plots wherein 0, 50, 100, 200, 400, and 800 nM EcoNth was incubated for 30 minutes at 3° C. with 100 nM of 4L, 5L, 5R, or N5R substrates in the presence of 50 mM sodium cyanoborohydride. Completed 35DHU reactions were separated by 12% SDS-PAGE; results from PhosphorImager analysis with calculated $\alpha$ values are plotted below each gel image. Completed 4L, 5L, 5R, and N5R reactions were mixed with an equal volume of 200 nM DAPI solution, incubated for 5 minutes at room temperature, and fluorescence was detected at 340 nm excitation/460 nm emission. Relative fluorescence readings to the 0 nM EcoNth sample were used to determine the concentration of ES complex at each enzyme concentration. Error bars representing the standard deviation from three independent experiments are shown on all points where the error was larger then the body of the symbol.

FIG. 3A shows an orientation of DAPI in the predicted binding location with BstNth and the 4L substrate. FIG. 3B shows the same orientations of DAPI with EcoFpg and the 4L substrate. FIG. 3C shows the same orientation of DAPI in the predicted binding location with BstNth and the 5R substrate. FIG. 3D shows the same orientations of DAPI with EcoFpg and the 5R substrate. Note the orientation of the minor groove at the DAPI binding site in each case. See Table 2 for a summary of predicted binding locations with each enzyme and substrate combination.

FIGS. 4A and 4D show a gel-shift and ES concentration plot wherein 0, 200, 400, 800, 1200, and 1600 nM EcoFpg was incubated for 30 minutes at 37° C. with 100 nM of 35DHU substrate in the presence of 50 mM sodium borohydride. FIGS. 4B-F show ES concentration plots wherein 0, 200, 400, 800, 1200, and 1600 nM EcoFpg was incubated for 30 minutes at 37° C. with 100 nM of 4L, 5L, 5R, or N5R substrates in the presence of 50 mM sodium borohydride. FIGS. 4G and 4J show a gel-shift and ES concentration plot wherein 0, 200, 400, 800, 1200, and 1600 nM EcoFpg was incubated for 30 minutes at 37° C. with 100 nM of 35DHU substrate in the presence of 100 mM sodium cyanoborohydride. FIGS. 4H-L show ES concentration plots wherein 0, 200, 400, 800, 1200, and 1600 nM EcoFpg was incubated for 30 minutes at 37° C. with 100 nM of 4L, 5L, 5R, or N5R substrates in the presence of 100 mM sodium cyanoborohydride. Completed 35DHU reactions were separated by 12% SDS-PAGE; results from PhosphorImager analysis with calculated $\alpha$ values are plotted below each gel image. Completed 4L, 5L, 5R, and N5R reactions were mixed with an equal volume of 200 nM DAPI solution, incubated for 5 minutes at room temperature, and fluorescence was detected at 340 nm excitation/460 nm emission. Relative fluorescence readings to the 0 nM EcoFpg sample were used to determine the concentration of ES complex at each enzyme concentration. Error bars representing the standard deviation from three independent experiments are shown on all points where the error was larger then the body of the symbol.

FIG. 6A shows relative fluorescence at each given enzyme concentration. FIG. 6B shows plotted ES concentrations, that were used to determine the $\alpha$ values by linear regression. Activity is simply defined as the percentage of determined $\alpha$ values ($100*\alpha$). NEIL1, solid circles; EcoNei, open circles.

DETAILED DESCRIPTION

Figure 1:
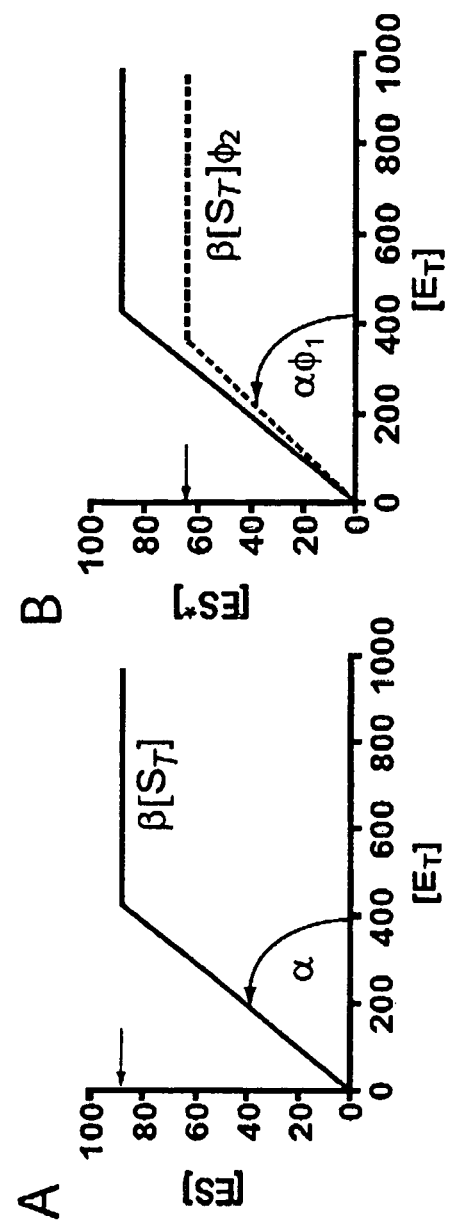
FIG. 1 is a panel of theoretical plots for active fraction determination.

The present invention relates to an assay technology that allows for rapid determination of bound nucleic-acid binding polypeptide in a given sample. The invention is based at least in part on the discovery of a novel assay for rapidly determining the active polypeptide fraction in a sample based on molecular accessibility of a DNA binding fluorescent reporter to a nucleic acid to which it binds. The invention relates, in part, to assays and methods for assessing the amount of bound nucleic acid-binding polypeptides in samples. The determination of the level of bound nucleic acid-binding polypeptide in a sample can be used to assess additional characteristics of binding in the sample, the nucleic acid-binding polypeptide, the binding polypeptide/nucleic acid interactions, etc.

Examples of characteristics that may be assessed using methods and kits of the invention include, but are not limited to: the rate of reaction between the binding polypeptide and nucleic acid, the type of reaction between the binding polypeptide and the nucleic acid, monofunctional versus bifunctional binding polypeptide classification (6-8), determination of the fraction of active molecule in an enzyme preparation (9, 10), reaction rate analysis (11, 12), glycosylase activity comparisons (13-15), ion-sulfur cluster domain analysis (16), the characterization of enzyme active site residues (10, 17-21), etc. Thus, assays and kits of the invention can be used to obtain information about the binding of nucleic acid binding polypeptides and the nucleic acid molecules to which they bind.

The present invention provides a method for assaying the amount of bound nucleic acid-binding polypeptide in a sample comprising the steps of: measuring the level of fluorescence in a sample comprising a nucleic acid, a nucleic acid binding fluorescent reporter, and a nucleic acid-binding polypeptide, wherein the nucleic acid sequence comprises a fluorescent reporter binding sequence and a binding polypeptide binding sequence positioned such that binding polypeptide bound to the nucleic acid inhibits binding of the fluorescent reporter to the nucleic acid and modulates the level of fluorescence in the sample, and comparing the level of fluorescence in the sample to a control level of fluorescence, wherein a difference in the level of fluorescence in the sample compared to the control level of fluorescence indicates the amount of bound nucleic acid-binding polypeptide in the sample.

The term "nucleic-acid binding polypeptide" ("binding polypeptide"), as used herein, can be any peptide, polypeptide or protein capable of binding a nucleic acid or an analog thereof. Nucleic-acid binding polypeptides according to the invention include, but are not limited to, monoclonal, polyclonal, engineered or fragment antibody, histone, telomere binding polypeptide, transcription factor, regulating polypeptide, receptor, ligand, enzyme, polypeptide complex, cell fragments, cell extracts and membrane fragments. In a certain embodiment of the invention, the nucleic-acid binding polypeptides are nucleic acid repair enzymes, including, but not limited to, base excision repair enzymes, mismatch repair enzymes, nucleotide excision repair enzymes, enzymes involved in recombination, enzymes involved in nonhomologous end joining, endo and exonucleoses. In certain embodiments the enzyme is a glycosylase, polymerase, nuclease, methyl transferase, or topoisomerase.

In specific embodiment of the invention the binding polypeptide is a DNA glycosylase. DNA glycosylases abstract the majority of single base lesions generated by reactive oxygen species (ROS) the as the initial step in the base excision repair pathway [for reviews, see (1,2)]. Mechanistically, these enzymes are classified by either the presence of an associated AP lyase activity (bifunctional), or the lack of this activity (monofunctional). Monofunctional glycosylases cleave the glycosyl bond via either an associative SN2 reaction utilizing an activated water molecule or a dissociative SN1-like mechanism. Bifunctional glycosylases employ an amine for nucleophilic (SN2) attack of the sugar backbone, proceeding through a Schiff base intermediate which can undergo a β-elimination that leads to cleavage of the lesion-containing strand. Enzymes whose mechanism proceeds through a transient Schiff base intermediate can be trapped by the addition of a reducing agent such as $NaBH_4$ or $NaCNBH_3$. Once covalently bound, trapped molecules no longer participate in the overall reaction resulting in stable polypeptide-DNA complexes.

Binding polypeptides of the present invention can be composed of amino acids joined to each other by peptide bonds or modified peptide bonds, i.e., peptide isosteres, and may contain amino acids other than the 20 gene-encoded amino acids. Binding polypeptides useful in the invention may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain more than one type of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to polypeptides such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992)).

Binding polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The binding polypeptides of the present invention are preferably provided in an isolated form, and preferably are substantially purified. A recombinantly produced version of a polypeptide, including the secreted polypeptide, can be substantially purified using techniques described herein or otherwise known in the art, such as, for example, by the one-step method described in Smith and Johnson, Gene 67:31-40 (1988). Polypeptides of the invention also can be purified from natural, synthetic or recombinant sources using techniques described herein or otherwise known in the art, such as, for example, antibodies of the invention raised against the polypeptides of the present invention in methods which are well known in the art.

The binding polypeptides of the invention may be isolated, secreted in supernatant, enzyme preparation or cellular extract, or reconstituted. In the present invention, a "secreted" polypeptide refers to those polypeptides capable of being directed to the ER, secretory vesicles, or the extracellular space as a result of a signal sequence, as well as those polypeptides released into the extracellular space without necessarily containing a signal sequence. If the secreted polypeptide is released into the extracellular space, the secreted polypeptide can undergo extracellular processing to produce a "mature" polypeptide. Release into the extracellular space can occur by many mechanisms, including exocytosis and proteolytic cleavage.

In the present invention, "isolated" refers to material removed from its original environment (e.g., the natural environment if it is naturally occurring), and thus is altered "by the hand of man" from its natural state. For example, an isolated polypeptide could be part of an enzyme preparation or a composition of matter, or could be contained within a cell, and still be "isolated" because that composition of matter, or particular cell is not the original environment of the polypeptide. An isolated sample may be a portion of a larger solution or preparation. For example, a sample may be obtained from an enzyme preparation and assayed using methods of the invention. One of ordinary skill in the art will recognize that by assaying a portion of a larger preparation or solution, the results regarding the level of binding, amount of active binding polypeptide, etc. obtained by assaying the sample can be extrapolated to provide such values for the original preparation that was the source of the sample.

By a binding polypeptide demonstrating a "functional activity" is meant, a polypeptide capable of binding a nucleic acid. A result of the binding is the interference with binding of a fluorescent reporter to the nucleic acid.

As used herein, a "sample" is any solution that comprises, or it is thought to comprise, nucleic-acid binding polypeptides. A sample may comprise isolated binding polypeptide and may be obtained from a cellular extract, a supernatant, an enzyme preparation, a reconstituted preparation, etc. In certain embodiments, the sample is obtained from a crude enzyme preparation or a cellular extract. It will be clear to those of ordinary skill in the art that the determination of the binding in a sample can be used to extrapolate the amount of active binding polypeptide in the source of the sample (e.g., the enzyme preparation, supernatant, cellular extract, etc).

"Nucleic-acids" according to the invention are oligonucleotides, polynucleotides or nucleotide arrays, including, but not limited to, DNA, RNA, cDNA, mMRA, and aptamers. A nucleic acid of the invention may also be a "modified oligonucleotide", including, but not limited to, a peptide nucleic acid (PNA), a locked nucleic acid (LNA), a phosphorothioate, or phosphorodiamidate morpholine. Nucleic acids according to the invention can be isolated from cells or tissue or can be artificially synthesized or modified using synthetic methods known in the art. Such nucleic-acid may contain chemical, enzymatic, or metabolic modifications to the nucleotides, nucleosides, the phosphodiester backbone, or the phosphodiester linkages. The nucleic acids according to the invention may comprise one or more telomere, methylated nucleic acid base, or damaged nucleic acid base. Damaged nucleic acid bases include but are not limited to 5,6-dihydrouracil, 7,8-dihydro-8-oxoguanine, 5,6-dihydroxy-5,6-dihydrothymine, 5-hydroxycytosine, 5,6-dihydrothymine, 5-hydroxyuracil, or 7,8-dihydro-8-oxoadenine. Examples of synthesis and modifications of nucleic acids are known to the skilled person and are described, for example, in "Protocols for Oligonucleotides and Analogs" Synthesis and Properties & Synthesis and Analytical Techniques, (S. Agrawal, Ed., Humana Press, Totowa, USA 1993).

Nucleic acids of the present invention can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. As discussed above polynucleotide may also contain one or more modified bases or DNA or RNA backbones modified for stability or for the incorporation of fluorescence reporter or binding polypeptide binding sequences. In specific embodiments, the nucleic acids of the invention are at least 5, at least 10, at least 15, at least 20, at least 25, at least 30, or at least 100 continuous nucleotides but are less than or equal to 1000 nucleotides in length.

Nucleic acids of the invention may include a "reporter-binding sequence" and a "binding polypeptide binding sequence." As used herein a "reporter-binding sequence" is a sequence of bases to which a fluorescent reporter normally can bind. As used herein, a "binding polypeptide binding sequence" is a sequence of bases in a nucleic acid to which a binding polypeptide normally can bind. In some embodiments, a nucleic acid molecule for use in an assay or kit of the invention (also referred to herein as a substrate nucleic acid) may be a nucleic acid molecule that includes at least one reporter-binding sequence and at least one binding polypeptide binding sequence. Those of ordinary skill in the art will be able to use routine methods to design, prepare, and use such nucleic acids (e.g., substrates) in methods and kits of the invention. Non-limiting examples of sequences that are specific for nucleic acid binding polypeptides and sequences that are specific for fluorescent reporter are provided in the Examples section.

In certain aspects of the invention the nucleic acid is DNA. In some embodiments of the invention, a DNA comprises one or more sequences that are preferably bound by the fluorescence reporter and/or the binding polypeptide. The nucleic acid according to the invention may comprise at least one sequence specific for fluorescent reporter binding. Alternatively or in addition, the nucleic acid according to the invention may comprise at least one sequence specific for polypeptide binding. In a certain aspect of the invention the fluorescent reporter binding sequence and the polypeptide binding sequence are positioned in the sequence of the nucleic acid such that the polypeptide bound to the polypeptide binding sequence interferes with the binding of the fluorescent reporter to the fluorescent reporter binding sequence. In certain embodiments, the binding polypeptide-bound nucleic acid is not detectably labeled, i.e., the fluorescent reporter is unable to bind the binding polypeptide-bound nucleic acid in a manner that would render it detectable.

As used herein the term, "interferes" means inhibits. A binding polypeptide of the invention that is bound to a substrate nucleic acid of the invention inhibits binding of a fluorescent reporter to that substrate nucleic acid. According to some aspects of the invention, a nucleic acid polypeptide is "bound" to a nucleic acid if the polypeptide inhibits the binding of the fluorescent reporter to the nucleic acid and thereby modulates the level of fluorescence in the sample. A binding polypeptide can be covalently or non-covalently bound to the nucleic acid substrate. A binding polypeptide can be covalently bound to the nucleic acid by an intermediate trapped by a trapping agent. A trapped intermediate can be, for example a Schiff base, and the trapping agent can be 2-deoxyribonolactone, oxanine, cis-Platinum, or a reducing agent such as the borohydride compounds, $NaBH_4$ or $NaCNBH_3$. As is understood by those of ordinary skill in the art, trapping an intermediate means the intermediate is "trapped" (e.g., held) on the nucleic acid at the position of the binding polypeptide binding sequence, thus inhibiting the ability of the fluorescent reporter to bind to its reporter-biding sequence on the substrate nucleic acid.

According to the invention "fluorescent reporter" is a fluorescent molecule whose fluorescence is modified when the reporter is bound to a nucleic acid, or a fluorophore-tethered nucleic acid or oligopeptide. Examples of fluorescent reporter include, but are not limited to 4',6-diamidino-2-phenylindole (DAPI), distamycin A, Hoechst 33258, netropsin, berenil, 2-hydroxystilbamidine, and chromomycin A3. It will be understood by those of ordinary skill in the art that a variety of different fluorophores may be used in conjunction with a reporter molecule of the invention. A suitable fluorophore for use in methods and kits of the invention includes a fluorophore whose fluorescence is modulated in assays of the invention by binding of binding polypeptide to substrate.

In specific embodiments of the invention, a fluorescent reporter is DAPI. The properties of 4',6-diamidino-2-phenylindole (DAPI) have been well studied for more than 30 years, from pH and ionic strength influences to the solved crystal structure of DAPI-DNA complexes. Similar to distamycin and its analogs, DAPI preferentially binds to the minor groove of AT-rich regions of double-stranded DNA. Due to its unique fluorescent characteristics DAPI has been employed successfully in various dye displacement assays.

As provided herein, a fluorescence energy signal includes any fluorescence emission, excitation, energy transfer, quenching or dequenching event or the like. Typically a fluorescence energy signal may be mediated by a fluorescent reporter bound to a nucleic acid in response to light of an appropriate wavelength. Briefly, and without wishing to be bound by theory, generation of a fluorescence energy signal generally involves excitation of a fluorophore (e.g., a fluorescent reporter DAPI bound to DNA) by an appropriate energy source (e.g., light of a suitable wavelength for the selected fluorescent reporter moiety, or fluorophore) that transiently raises the energy state of the fluorophore from a ground state to an excited state. The excited fluorophore in turn emits energy in the form of detectable light typically having a different (e.g., usually longer) wavelength from that used for excitation, and in so doing returns to its energetic ground state. The methods of the present invention contemplate the use of any fluorescence energy signal, depending on the particular fluorescent reporter, nucleic acid and detection instrumentation, which may be selected readily and without undue experimentation according to criteria with which those having ordinary skill in the art will be familiar (Haugland, Handbook of Fluorescent Probes and Research Chemicals-6th Ed., 1996, Molecular Probes, Inc., Eugene, Oreg.; and references cited therein.). A change in the fluorescence energy signal of a fluorescent reporter in a sample may indicate that binding of a fluorescent reporter has been modulated (e.g., inhibited) by binding of a binding polypeptide to the nucleic acid (e.g., to the substrate). In some embodiments, binding of a binding polypeptide to a nucleic acid (substrate) may inhibit the total level of binding of a fluorescent reporter to the nucleic acid in a sample by at least about 1%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%.

Modulation of the fluorescent signal of a reporter nucleic acid may be detected as a change in the level of the fluorescent signal. A signal is modulated if it differs by at least about 1%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% as compared to a control level of fluorescence signal. In some embodiments, a control level of fluorescence may be the level of fluorescence that results when a fluorescent reporter binds to a nucleic acid sequence (substrate) in the absence a binding polypeptide. In certain embodiments, a control level of fluorescence is the level of fluorescence that results when a fluorescent reporter binds to a nucleic acid sequence in the presence of a known level of functional nucleic acid-binding polypeptide. Thus, in some embodiments, the level of fluorescence in a sample assayed using methods of the invention can be compared to a standard curve. An example of a control or standard curve, although not intended to be limiting, may include one or more measurements of the different levels of fluorescence associated with different amount of a nucleic acid-binding polypeptide bound to substrate. Such a standard curve may be used as a control level with which to compare fluorescence in a sample assayed using methods of the invention and can therefore be used to assess the level of fluorescence in the sample and for determining the corresponding level of binding polypeptide in the sample. Those of ordinary skill in the art will know how to prepare and utilize standard curves for use in methods and with kits of the invention.

As will be recognized by those of ordinary skill in the art, if in an assay of the invention, the level of fluorescence decreases in a test sample compared to the level in a control sample that comprises no binding polypeptide, it indicates that the test sample contains binding polypeptide that is bound to the nucleic acid (substrate) and is interfering with binding between the fluorescent reporter and the nucleic acid in the test sample. Thus, in some embodiments of the invention, an increase in binding polypeptide bound to the nucleic acid results in a decrease in fluorescence in the sample.

As used in the methods of the invention, a control level of fluorescence may be a predetermined value, which can take a variety of forms. It can be a single cut-off value, such as a median or mean. It can be established based upon comparative groups, such as in groups having a set amount of nucleic acid, nucleic acid-binding polypeptide, and fluorescent reporter, and groups having different amounts of one or more of those constituents. It will also be understood that controls according to the invention may be levels of fluorescence obtained from samples of materials tested in parallel with the experimental materials. Examples include samples that include a nucleic acid and a fluorescent reporter with a predetermined amount of the nucleic acid-binding polypeptide (e.g., zero nucleic-acid binding peptide), and any other predetermined amount of nucleic acid-binding polypeptide, volume, temperature, etc.

It will be recognized by the skilled artisan that the methods and compositions of the invention are suitable for use in high throughput applications and can be easily modified for such use. For example, the assays described in the examples may be readily used in a microplate format, such as 96-well plates.

According to the invention compositions are provided that comprise a nucleic acid comprising a fluorescent reporter binding sequence and a binding polypeptide binding sequence positioned such that binding polypeptide bound to the nucleic acid may inhibit the binding of the fluorescent reporter to the nucleic acid. Such composition may optionally further comprise a fluorescent reporter or a binding polypeptide. Such a composition may be used according to the methods of the invention, by mixing it with a sample comprising, or believed to comprise a binding polypeptide. In some embodiments, a control composition may include a substrate and a fluorescent reporter and may not include any binding polypeptide. Compositions of the inventions may be provided in containers in the kits, further may comprise instructions for use. The instructions can include directions for carrying out assays according to the methods of the invention.

According to a certain aspect of the invention the methods and compositions of the invention can be used to determine whether an agent or compound modulates the activity (e.g., binding) of a nucleic acid binding polypeptide by measuring the amount of fluorescence in the a sample comprising the agent, a nucleic acid, a nucleic acid binding fluorescent reporter, and the nucleic acid-binding polypeptide. For example, such an assay can used to identify inhibitors of enzymes, such as DNA repair enzymes. Such as assay, according to the methods of the invention may be used to identify small molecules that are therapeutic candidates, based on their capacity to modulate binding polypeptide nucleic acid binding.

Thus, methods and compositions of the invention may be useful in methods of screening for candidate agents (e.g., candidate compounds) that modulate binding of binding polypeptides to nucleic acids. Methods can include mixing the candidate agent with a sample and using assay methods of the invention to determine whether the candidate agent alters the binding of binding polypeptide using a determination of modulation in fluorescence versus a control sample to which the candidate agent was not added. An increase in the amount of fluorescence in the presence of the candidate agent may mean that the candidate agent reduces binding of the binding polypeptide to the nucleic acid substrate thus permitting more fluorescent reporter binding to the nucleic acid substrate. Similarly, a decrease in the amount of fluorescence in the presence of the candidate agent may mean that the candidate agent increase binding of the binding polypeptide to the nucleic acid substrate thus reducing the amount of fluorescent reporter that can bind to the nucleic acid substrate in the sample.

An assay mixture in such embodiments comprises a candidate agent. The candidate agent is preferably an antibody, a small organic compound, or a polypeptide, and accordingly can be selected from combinatorial antibody libraries, combinatorial protein libraries, or small organic molecule libraries. Typically, pluralities of reaction mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents encompass numerous chemical classes, although typically they are organic compounds, proteins or antibodies (and fragments thereof that bind antigen). In some preferred embodiments, the candidate agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as polypeptides, saccharides, fatty acids, sterols, isoprenoids, purines, pyrimidines, derivatives or structural analogs of the above, or combinations thereof and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random polypeptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known agents may be subjected to directed or random chemical modifications such as acylation, alkylation, esterification, amidification, etc. to produce structural analogs of the agents.

Methods and compositions of the invention may be useful for biochemical studies including, but are not limited to: bifunctional vs. monofunctional classification, determination of the fraction of active molecules in enzyme preparations, reaction rate analyses, enzyme activity comparisons, iron-sulfur cluster domain analysis, and the characterization of enzyme active site residues.

It will be appreciated by the skilled artisan that the methods and compounds of the invention can be used for diagnostic purposes. If a given disorder is characterized by a change of nucleic acid binding properties of a certain nucleic acid binding polypeptide, such a disorder may be diagnosed by identifying the deficient binding polypeptide according to the methods of the invention.

It will also be appreciated by the skilled artisan that the methods and compounds of the invention can be used to screen for binding polypeptides that are therapeutic candidates based on their nucleic acid binding properties.

The invention is not limited in its application to the details of the structure and function of the invention set forth in the following description or illustrated in the appended figures of the drawing. The invention is capable of other embodiments and of being practiced or carried out in various ways. Also, it is to be understood that the phraseology and terminology used herein is for the purpose of description and should not be regarded as limiting. The use of terms such as "including," "comprising," or "having" and variations thereof herein is meant to encompass the item listed thereafter and equivalents thereof as well as additional items.

The present invention is further explained by the following examples, which should not be construed by way of limiting the scope of the present invention.

EXAMPLES

Example 1

Rapid Determination of the Active Fraction of DNA Repair Glycosylases

Introduction

A novel assay has been developed for rapidly determining the active protein fraction in a sample based on molecular accessibility of a fluorescent DNA minor groove binder, 4',6-diamidino-2-phenylindole (DAPI). DAPI was used as a fluorescent reporter molecule to rapidly differentiate the number of bound vs. unbound enzymes to damaged oligonucleotides following polypeptide-DNA cross-linking. Several 5,6-dihydrouracil-containing (DHU) DNA substrates were designed with sequence-dependent DAPI binding sites to which base excision repair glycosylases were covalently trapped by reduction. Trapped complexes impeded the association of DAPI in a manner dependent on the enzyme used and the location of the DAPI binding site in relation to the lesion. Of the sequences tested, one was shown to give an accurate measure of the fraction of active molecules for each enzyme tested from both the Fpg/Nei family and HhH-GPD Nth superfamily of DNA glycosylases. The validity of the approach was demonstrated by direct comparison with current gel-based methods. Additionally, the results are supported by in silico modeling based on available crystal structures.

Non-obligate organisms possess repair systems responsible for the maintenance of genomic DNA in the presence of cellular reactive oxygen species (ROS). The majority of single-base lesions generated by ROS are abstracted by DNA glycosylases as the initial step in the base excision repair pathway [for reviews, see (1,2)]. Mechanistically, these enzymes are classified by either the presence of an associated AP lyase activity (bifunctional), or the lack of this activity (monofunctional). Monofunctional glycosylases cleave the glycosyl bond via either an associative $S_N2$ reaction utilizing an activated water molecule or a dissociative $S_N1$-like mechanism. Bifunctional glycosylases employ an amine for nucleophilic ($S_N2$) attack of the sugar backbone, proceeding through a Schiff base intermediate that can undergo a β-elimination that leads to cleavage of the lesion-containing strand [for reviews, see (3,4)]. Enzymes whose mechanism proceed through a transient Schiff base intermediate can be trapped by the addition of a reducing agent such as $NaBH_4$ or $NaCNBH_3$ [for a review, see (5)]. Once covalently bound, trapped molecules no longer participate in the overall reaction resulting in stable protein-DNA complexes.

The properties of 4',6-diamidino-2-phenylindole (DAPI) have been well studied for more than 30 years, from pH and ionic strength influences (23,24) to the solved crystal structure of DAPI-DNA complexes (25,26). Similar to distamycin and its analogs, DAPI preferentially binds to the minor groove of AT-rich regions of double-stranded DNA (24, 27-31). DAPI has been employed successfully in various dye displacement assays (32,33). The studies set forth herein utilize a novel approach for using DAPI as a fluorescent reporter molecule to rapidly differentiate the number of bound vs. unbound enzymes to damaged oligonucleotides following protein-DNA cross-linking. These methods are useful for determining the fraction of active molecules in enzyme preparations and the technique is equally applicable to additional studies such as bifunctional vs. monofunctional classification, determination of the fraction of active molecules in enzyme preparations, reaction rate analyses, glycosylase activity comparisons, iron-sulfur cluster domain analysis, and the characterization of enzyme active site residues.

Methods

DNA Substrates.

Oligonucleotide substrates were purchased from Midland Certified Reagent Co. (Midland, Tex.) and were PAGE purified prior to use. All gel-based comparisons were performed with the following double stranded substrate: (35DHU) 5'-TET-tgtcaatagcaagnggagaagtcaatcgtgagtct-3' (SEQ ID NO:1) where TET represents the fluorescent label 6-tetrachlorofluorescein and n=5,6-dihydrouracil (DHU). Molecular accessibility DAPI-based experiments were performed with the following double-stranded substrates: (4L) 5'-gc-cccgccaattnccgccgccgcc-3' (SEQ ID NO:2), (5L) 5'-gc-cccgccaattcnccgccgccgcc-3'(SEQ ID NO:3), (5R) 5'-gc-cccgccgccccgccnaattccgccgccgcc-3' (SEQ ID NO:4), and (N5R) 5'-gccccgccgccccgccncaattccgccgccgcc-3' (SEQ ID NO:5) where n=either DHU for damaged substrates or cytosine for non-damaged controls. All complementary strands contained a G residue across from DHU (or across from the cytosine in controls—e.g. Watson-Crick base pairing) and were annealed in 50 mM Tris-HCl (pH 8.0), 50 mM NaCl by heating to 94° C. for 2 minutes and slowly cooling to 4° C. over the period of 1 hour in a Perkin Elmer DNA Thermal Cycler 480. In each case the ratio of damaged to complementary strand during annealing was 1:1.1. Note that the DAPI-based oligonucleotides all differ in location of the AT-rich region in relation to the damaged base.

Purification of Enzymes.

*Escherichia coli* endonuclease III (EcoNth), formamidopyrimidine-DNA glycosylase (EcoFpg), endonuclease VIII (EcoNei), and its human ortholog (NEIL1) were purified by either the pET system (Novagen) or IMPACT CN system (New England Biolabs, Ipswich, Mass.). A detailed protocol for cloning and expression of each of these recombinant polypeptides has been previously described (34).

Trapping of Schiff Base Intermediates.

EcoNth, EcoFpg, EcoNei, and NEIL1 were incubated for 30 minutes at 37° C. with 100 nM DHU:G-containing substrates at final concentrations of 50, 100, 200, 400, 800, 1200, or 1600 nM, in the presence of either 50 or 100 mM sodium borohydride ($NaBH_4$) or sodium cyanoborohydride (NaCNBH$_3$), as described in the Figures. Borohydride compounds were dissolved fresh for each independent experiment (one substrate and series of enzyme dilutions) as 1.25× stocks in Milli-Q water. Reactions were initiated by simultaneous addition of enzyme and borohydride solution to annealed substrates utilizing separate multi-pipettes in a 96-well format to a final volume of 100 µL. Except for EcoFpg trapping with sodium cyanoborohydride, the final buffer for each reaction contained 10 mM Tris-HCl (pH 8.0), 60 mM $Na^+$, and either 50 mM $BH_4^-$ or $CNBH_3^-$. In the former case, the final buffer contained 10 mM Tris-HCl (pH 8.0), 110 mM $Na^+$, and 100 mM $CNBH_3^-$.

For gel-based substrates, completed reactions were mixed with a dye-free SDS loading buffer (50 mM Tris-HCl (pH 6.8), 100 mM dithiothreitol, 4% SDS, 10% glycerol), heated to 90° C. for 5 minutes, separated by 12% SDS-PAGE, and visualized by PhosphorImager analysis (Bio-Rad Molecular Imager FX) (Bio-Rad Laboratories, Hercules, Calif.). For all other substrates, an equal volume of 200 nM DAPI in 10 mM Tris-HCl (pH 8.0) and 50 mM NaCl was added and incubated for 5 minutes at room temperature prior to fluorescence detection. Final concentrations of the fluorescence effecting molecules at the time of detection in these experiments were 100 nM DAPI, 50 nM substrate, and 25-800 nM enzyme.

Fluorescence Measurements.

Fluorescence readings were made on a Synergy HT Multi-Detection Microplate Reader (BIO-TEK) using a tungsten-halogen lamp and 360/40 bandpass excitation filter in conjunction with a 460/40 emission filter. Corning Half Area, NBS treated (Nonbinding Surface), Black, 96-well Microplates plates (Corning #3686) were used for all DAPI-based experiments. The combination of enzymes, DNA, and DAPI were all shown to contribute linearly to changes in the overall fluorescence based on the range of concentrations used; there was therefore no need to correct for the inner filter effect.

Sodium Cyanoborohydride Optimization.

Trapping and fluorescence detection were performed essentially as described above with 100 nM 4L substrate, 200 nM EcoFpg, and final buffer concentrations of 10 mM Tris-HCl (pH 8.0), 60 mM $Na^+$, and 0-200 mM $CNBH_3^-$. The ionic strength contribution from sodium ions was held constant by varying the amount of the following compounds added to each reaction: sodium chloride, sodium cyanoborohydride, and/or tetrabutylammonium cyanoborohydride. Fluorescence was normalized to the first reading and plotted as a 36 segment cubic spline curve using Prism 4 (GraphPad Software, San Diego, Calif.).

Data Analyses: Determining the Active Fraction of Molecules.

Given a sufficiently high concentration of trapping reagent, and a sufficiently long incubation time, the quantity of ES complex is related to the quantity of total enzyme added, $E_T$, and total substrate added, $S_T$, by the equation: ES=min($\alpha E_T$, $\beta S_T$) where $\alpha$ is the active enzyme fraction, P is the active substrate fraction (fraction cleavable), and min is the minimum function. Furthermore, holding $S_T$ constant while varying $E_T$ can be depicted graphically (FIG. 1A) where the rising slope is equivalent to $\alpha$, the plateau is equivalent to $S_T*\beta$, and the breakpoint is defined by the relation: $S_T=(\alpha/\beta)E_T$. Therefore, by varying $E_T$ from below to well above the constant $S_T$ concentration, the active enzyme fraction can be determined by linear regression of all points falling below the $E_T$ breakpoint concentration. The decision to include or exclude a given point pre-breakpoint is simply made so as to minimize the root-mean squared deviation from both the pre-breakpoint regression and the post-breakpoint best-fit line with a slope of zero.

For gel-based assays, the active enzyme fraction was determined following phosphorimager analysis from the relative amounts of trapped to non-trapped DNA by the a value method described above. For the molecular accessibility assays, the active fraction was determined from relative fluorescence values also using the α value method (note that an increase in trapped enzyme complex translates to a decrease in detected fluorescence). We hypothesized that the location of the DAPI binding site in relation to the trapped enzyme would affect the total detected fluorescence, possibly leading to a lower quantity of ES complex detected on some sequences. This is depicted in FIG. 1B such that the determination of trapped complex can be described as: ES*=min $(\alpha E_7 \Phi_1, \beta S_7 \Phi_2)$ where $0 \leq \Phi_{1,2} \leq 1$ is an accessibility parameter and ES*≤ES. Complete association of DAPI, independent of the quantity of trapped ES complex, would have an accessibility parameter equal to 0. In contrast, association which is perfectly dependent on the quantity of trapped ES complex would have accessibility parameter of 1, and therefore ES* equals ES. In this study, we show the existence of an oligonucleotide sequence (4L) where $\Phi$ approaches 1 for several DNA glycosylases from different phylogenetic families.

Molecular Modeling.

Figure 3:
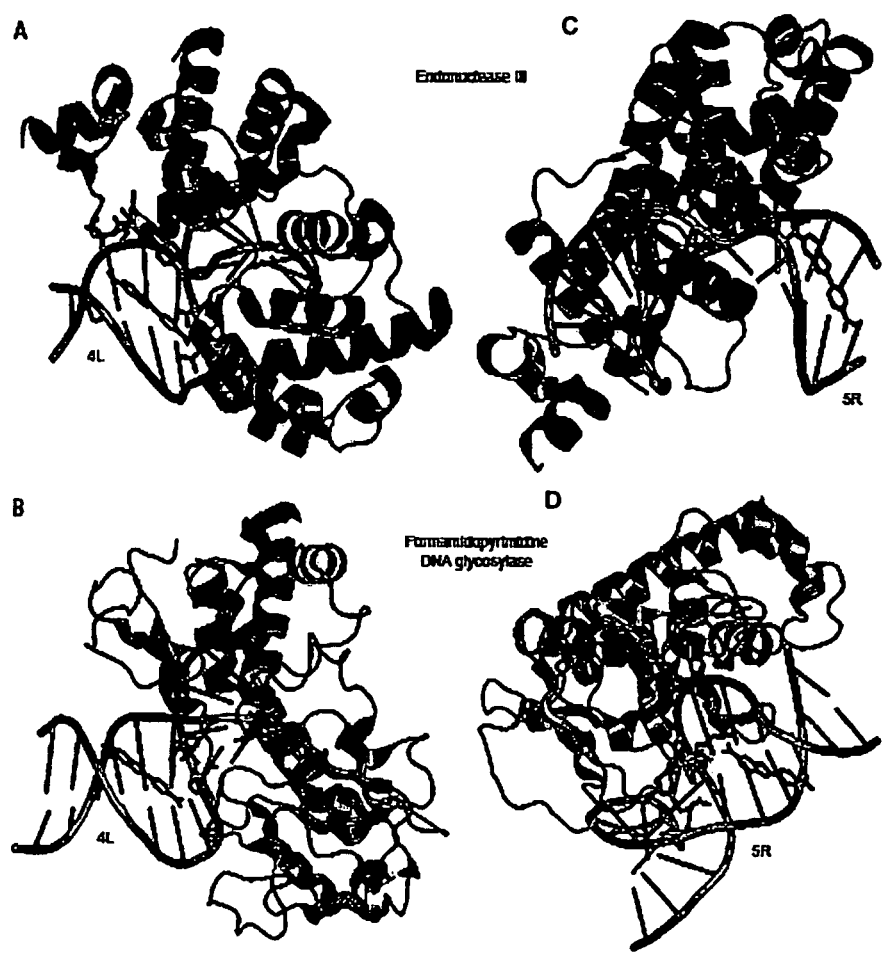
FIG. 3 shows molecular modeling renderings of BstNth and EcoFpg with DAPI.

Modeling for the illustrations shown in FIG. 3, and for the results listed in Table 2 was performed using the PyMol Molecular Graphics System (DeLano, W. L., 2002, www.pymol.org) as follows: two published structures of DAPI-DNA complexes, AATT localized from 1D30.pdb (25) and the proposed ATTG shifted localization from 432D.pdb (26,35), were molecularly superimposed onto the published BstNth and EcoFpg Schiff base intermediate-trapped structures 1ORN.pdb (36) and 1K82.pdb (37), respectively.

Alignment was made using the phosphate backbone of the AATT region of the DAPI structures and the corresponding phosphate backbone of each enzyme-DNA structure for both possible orientations of DAPI (due to non-symmetry of the dye and target). The pair_fit command was used to minimize the root mean square deviation (RMSD) of each atom in the alignment. In total, the 32 modeled structures were fit by alignment of 66, 85, or 88 atoms with RMSD values of the fit ranging from 0.765 to 1.815 Angstroms.

Results

Fluorescence of DAPI-Bound DNA Substrates.

Each of the 4L, 5L, 5R, and N5R substrates, along with their non-damaged counterparts, were initially tested for their ability to associate with DAPI and thereby affect the detected fluorescence. As can be seen in Table 1, each of the sequences showed a significant increase in fluorescence over background. In the absence of DNA, there was only a small increase in fluorescence from the addition of DAPI, as would be expected. The differences in fluorescence for each of the DAPI bound substrates are presumably due to both, sequence context and experimental variations in DNA concentration. For example, the 4L sequence is expected to have a lower total fluorescence due to the importance of the 3' nucleotide following the 5'-AATT-3' binding sequence in regards to fluorescence intensity (38). Due to the fact that the molecular accessibility assay is based on relative fluorescence, these differences are inconsequential. Non-damaged substrates, where the DHU base is replaced with cytosine, were also tested; the fluorescence levels of these substrates were statistically equal to their damaged counterparts with the exception of the 4L(–) context, which showed an expected increase from the introduction of cytosine in the 5'-AATTC-3' sequence.

TABLE 1

Fluorescence of DAPI binding to double stranded DNA. 50 nM of each double stranded DNA was incubated with 100 nM DAPI in 10 mM Tris-HCl (pH 8.0) and 50 mM NaCl for 5 minutes at room temperature and fluorescence was detected on a Synergy HT Multi-Detection Microplate Reader. x = DHU. All complementary strands contained a G residue across from DHU. See Methods section for the complete oligonucleotide sequences.

| dsDNA   | Subsequence       | DAPI | FI[†]        |
|---------|-------------------|------|--------------|
| 4L      | 5'-ccaattxc-3'    | +    | 55.2 ± 2.8   |
| 4L (–)  | 5'-ccaattcc-3'    | +    | 62.4 ± 2.3   |
| 5L      | 5'-ccaattcx-3'    | +    | 65.9 ± 2.6   |
| 5L (–)  | 5'-ccaattcc-3'    | +    | 63.3 ± 4.3   |
| 5R      | 5'-cxaattcc-3'    | +    | 69.5 ± 2.9   |
| 5R (–)  | 5'-ccaattcc-3'    | +    | 63.7 ± 3.4   |
| N5R     | 5'-xcaattcc-3'    | +    | 60.7 ± 3.0   |
| N5R (–) | 5'-ccaattcc-3'    | +    | 60.7 ± 3.1   |
|         | –n/a              | +    | 5.0 ± 0.4    |
|         | –n/a              | –    | 2.7 ± 0.1    |

[†]FI = Fluorescence Intensity x10$^{-3}$.

EcoNth: DAPI Accessibility Emulates Gel-Based Results.

Figure 2:
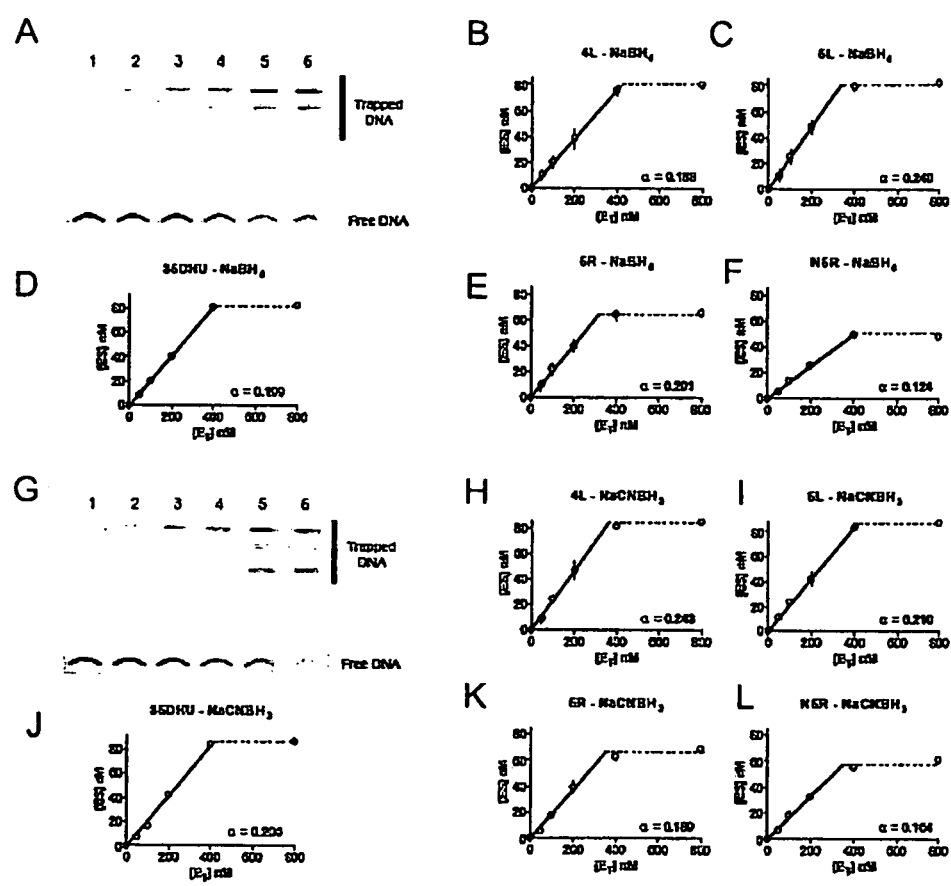
FIG. 2 is a panel of gel-shifts and ES concentration plots showing EcoNth active fraction determination by gel-based and molecular accessibility assays.

In order to validate the results of the molecular accessibility assay, the active fraction of a preparation of EcoNth was first determined via traditional gel-based methods. As shown in FIGS. 2A and 2C, the α values were determined to be 0.199 and 0.206 for experiments using NaBH$_4$ and NaCNBH$_3$ as reducing agents, respectively. This corresponds to an active fraction of approximately 20%. The β value, was determined to be approximately 0.8, which is consistent with the active fraction of substrates used. For each data plot, the α and β values were calculated as depicted in FIG. 1, and as described in the Methods Section. The total amount of trapped complex was determined from the sum of each shifted band in a given lane. The occurrence of multiple gel-shifted bands is a consequence of the trapping of intermediates along the reaction pathway and their separation via SDS-PAGE (22). It should be noted that the molecular accessibility assay will not distinguish between reaction intermediates; a single fluorescent reading for each enzyme concentration point is generated for all trapped complexes. For this reason, considering the difficulties associated with accurately measuring pixel intensities, the DAPI-based approach is more accurate.

Results of the molecular accessibility assay for each of the sequence contexts and reducing agents used are shown in FIGS. 2B and 2D. The calculated α values for the 4L, 5L, and 5R sequences ranged from 0.188 to 0.243 giving an active fraction range of approximately 19-24%, consistent with the gel-based results. The calculated α values for the N5R sequence were lower, giving associated active fractions of approximately 12% and 16%, presumably due to the ability of DAPI to associate with the EcoNth-NSR trapped complex. Interestingly, both the 5R and N5R sequences showed lower then expected β values, suggesting at least some association of DAPI with the EcoNth-5R trapped complex as well.

In order to further elucidate the above results, DAPI was modeled into its predicted binding locations for each complex using a *Bacillus stearothermophilus* endonuclease III trapped intermediate, as described in the methods section. Association of DAPI with a trapped complex is modulated by two main factors, steric hindrance between any "close contacts" and orientation of the minor groove at the DAPI binding site in relation to the polypeptide. FIG. 3A shows two predicted binding locations: one orientation of DAPI bound to the 5'-AATT-3' site with BstNth-4L and one with BstNth-5R. In the 4L sequence the minor groove where DAPI binds is on an internal face, protected by the enzyme. With the 5R sequence however, the minor groove is exposed such that DAPI association can only be inhibited by steric hindrance from close amino acids. The top half of Table 2 summarizes the BstNth modeling results with regard to close contacts and minor groove location, for each predicted binding mode and orientation. The shortest distance in Angstroms between any two atoms of bound DAPI and BstNth are listed for each of the two structure-solved binding modes. As can be seen, steric hindrance predicts that the 4L, 5L, and possibly 5R sequences should accurately determine the active fraction. Additionally, both the 4L and 5L sequences benefit from having the minor groove where DAPI binds in a protected location. These modeling data support the results shown in FIGS. 2B and 2D, providing further evidence of the validity of this assay.

EcoFpg: DAPI Accessibility Emulates Gel-Based Results.

Figure 4:
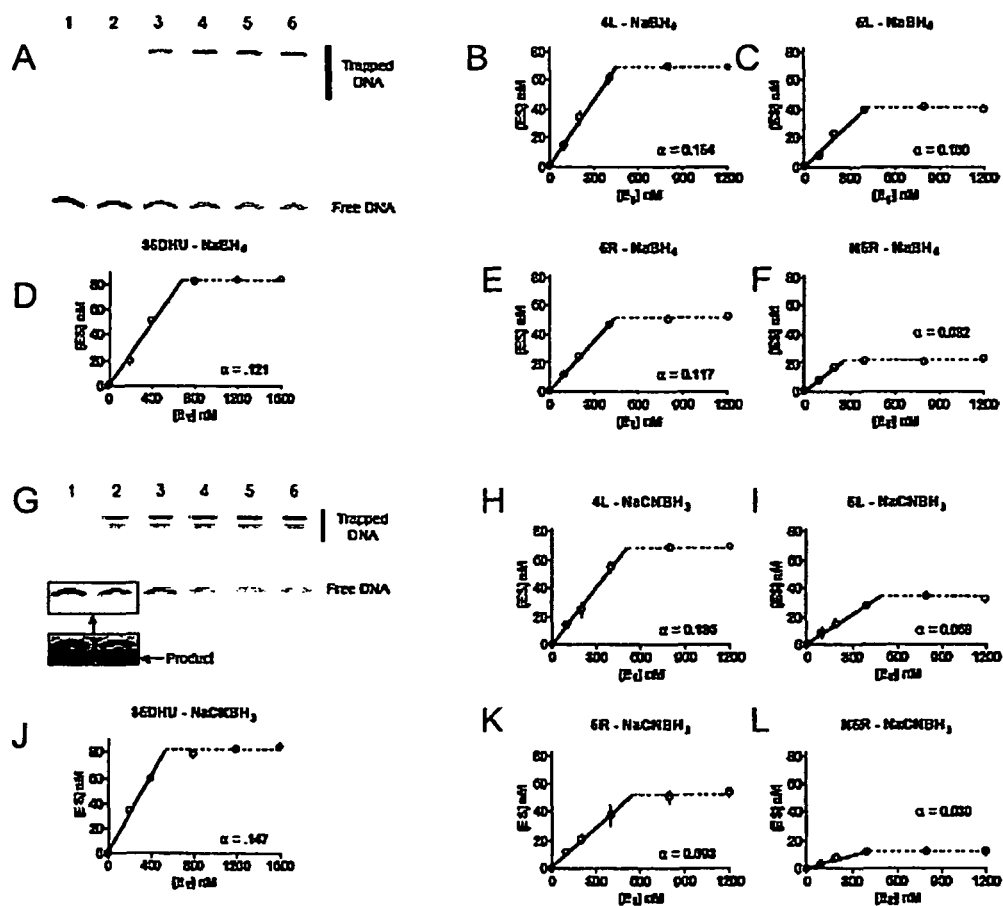
FIG. 4 is a panel of gel-shifts and ES concentration plots showing EcoFpg active fraction determination by gel-based and molecular accessibility assays.

Similar to above, the active fraction of a preparation of EcoFpg were also determined via traditional gel-based methods. As shown in FIGS. 4A and 4C, the α values were determined to be 0.121 and 0.147 depending on the reducing agent used—corresponding to an active fraction of approximately 13%. The β value was again approximately 0.8. Notably, when using 100 mM sodium cyanoborohydride as a reducing agent (FIG. 4C), a small amount of product was generated. The quantity of product is small enough so that its inclusion or exclusion during analysis only affects the determined α value by approximately 1.5%. However, the importance of limiting product generation is discussed in detail below. Results of the molecular accessibility assay for each of the sequence contexts and reducing agents used with EcoFpg are shown in FIGS. 4B and 4D. The calculated α values for the 4L sequence were 0.154 and 0.136 giving an active fraction of approximately 14%, consistent with the gel-based results. The calculated α values for the 5R sequence were slightly lower giving an approximate 11% active fraction, and both the 5L and N5R sequences were significantly lower. The apparent β values were significantly lower for the 5L, 5R and N5R sequences, suggesting increased association of DAPI with the EcoFpg-DNA trapped complex, and therefore a smaller accessibility parameter, Φ. The apparent β value for the 4L sequence was approximately 0.7 in these experiments. Re-testing with EcoNth verified that the 10% drop in β value for the 4L substrate was accurate, and was presumably caused from prolonged storage of the annealed, DHU-containing substrate at 4° C.

As was done with BstNth, modeling of DAPI into the predicted binding locations for each of the trapped EcoFpg-DNA complexes was performed as described in the Methods section and is illustrated for two cases in FIG. 3B. Once again, the 4L sequence protects the minor groove of the drug binding site, while the 5R sequence exposes the 5'-AATT-3' minor groove. The bottom half of Table 2 summarizes the EcoFpg modeling results for all predicted binding sites, for each DNA sequence. Interestingly, only the enzyme-trapped 5R sequence predicts any steric hindrance with regard to DAPI binding. For each of the other sequences there is at least one orientation of DAPI with significant steric freedom. This includes the 4L sequence, which was already shown to accurately determine the active fraction of enzyme in FIG. 4. This result highlights the importance of the orientation of the minor groove at the DAPI binding site, and predicts the practicality of using the 4L substrate for numerous DNA glycosylases regardless of active site binding differences. Noting the importance of the minor groove orientation, the modeling data again support the molecular accessibility assay results.

TABLE 2

Molecular modeling summary of DAPI bound to trapped enzyme-DNA complexes.

| Complex | AATT | ATTG | Minor Groove |
| --- | --- | --- | --- |
| Nth - 4L | 1.54, 1.70* | 1.85, 1.50* | internal face |
| Nth - 5L | 2.36, 2.55 | 1.56, 2.09 | internal face |
| Nth - 5R | 2.13*, 2.32 | 2.21*, 3.10 | external face |
| Nth - N5R | 2.51, 4.41 | 2.96, 7.87 | external face |
| Fpg - 4L | 4.97, 4.51* | 6.26, 1.58* | internal face |
| Fpg - 5L | 5.01, 7.33 | 4.09, 10.8† | internal face |
| Fpg - 5R | 0.72*, 1.33 | 1.19*, 3.23 | external face |
| Fpg - N5R | 2.54, 4.67 | 1.51, 7.16 | external face |

The distance in angstroms is shown for the two closest atoms between DAPI and either BstNth or EcoFpg. Both of the known DAPI binding modes based on crystal structure data, AATT and ATTG, for each of the two possible DAPI orientations (separated by commas) are listed. The last column specifies the orientation of the minor groove where DAPI binds, in relation to the trapped polypeptide. See Methods section for details describing the creation of these modeling summaries.
†externally facing exception due to distance from polypeptide.
*orientation unlikely to occur due to the disruption of one or more hydrogen bonds with the cleaved DNA base.

Optimizing the Concentration of Reducing Agent.

Figure 5:
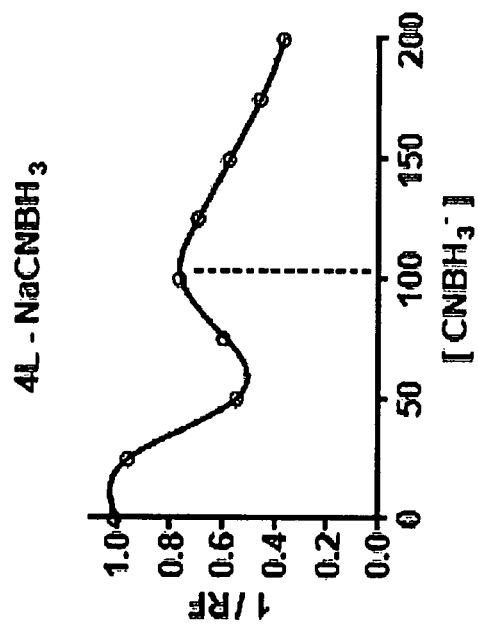
FIG. 5 is a graph showing the reducing agent optimization with the molecular accessibility assay. 200 nM EcoFpg was incubated for 30 minutes at 37° C. with 100 nM 4L substrate in the presence of 0-200 mM cyanoborohydride ion. Tetrabutylammonium cyanoborohydride was used at high concentrations to maintain similar ionic strengths in each reaction. Fluorescence was normalized to the first reading and plotted as inverse relative fluorescence vs. $CNBH_3^-$ concentration on a cubic spline curve.

Optimizing the concentration of reducing agent used is an important step for any trapping assay. It is, however, of particular importance for accurately determining the active fraction by DAPI association. Fully cleaved 4L substrate shows approximately one-half the maximal fluorescence compared to uncleaved substrate, due to a higher rate of DAPI dissociation. The increased dissociation rate of the dye is presumably caused by the single-strand nick 3' of the binding site. Nevertheless, the effect of this characteristic would be an increase in apparent trapped complex in situations where significantly high quantities of product are allowed to form, leading to an artificially high α value and lower β value. To avoid this, the accessibility assay itself can be used to quickly optimize the concentration of reducing agent. FIG. 5 shows a typical optimization experiment where sodium cyanoborohydride concentration is optimized for one concentration of EcoFpg. As the concentration of reducing agent initially increases we see a substantial drop in the apparent concentration of trapped complex. This drop is expected based on the fact that a higher percentage of active enzyme molecules are being trapped before they are able to turnover a significant amount of product. Beyond 50 mM NaCNBH$_3$ we see that there is an inflection point in the graph where increases in reducing agent concentration more efficiently lead to trapped complexes while limiting the production of product. The final inflection point at ~100 mM NaCNBH$_3$ is the optimal concentration for this reducing agent with this specific enzyme; higher concentrations prove inhibitory. The magnitude of each inflection point is specific to the enzyme used and to the active fraction of the enzyme in the preparation being tested. Finally, one should note the importance of maintaining ionic strength even at higher reducing agent concentrations, by using compounds such as tetrabutylammonium cyanoborohydride.

As shown in FIG. 5, the optimal cyanoborohydride concentration was determined to be 100 mM. This concentration was used for the experiments shown in FIG. 4C, yet a small amount of product was still detected. Therefore, the use of a stronger reducing agent like NaBH$_4$ recommended. While one could use NaBH$_4$ exclusively, the concurrent use of NaCNBH$_3$ provides a beneficial level of redundancy and comparisons between the two provide good evidence concerning the generation of a significant quantity of product.

DAPI Accessibility with Different Enzyme Preparations.

Figure 6:
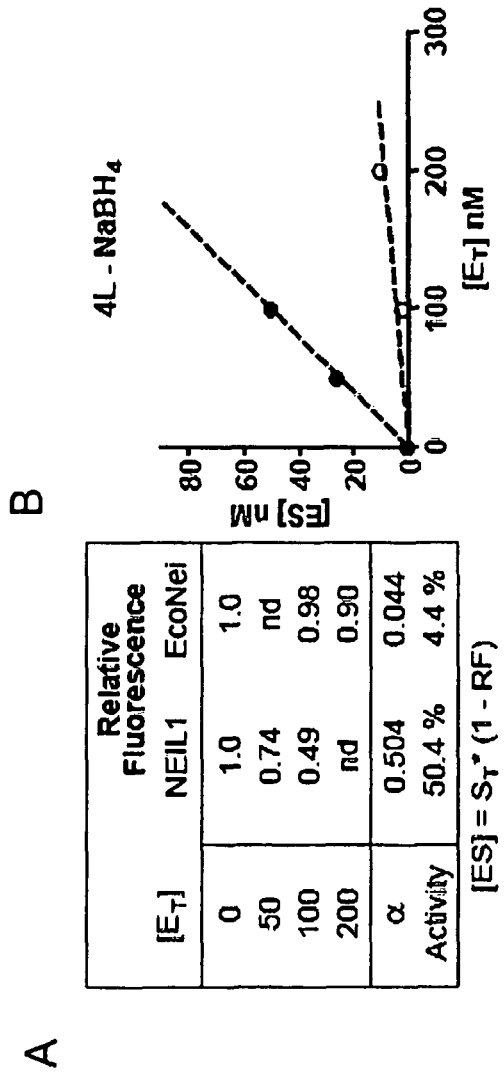
FIG. 6 is a table and an ES concentration plot showing NEIL1 and EcoNei active fraction determination by the molecular accessibility assay. 50 and 100 nM NEIL1 and 100 and 200 nM EcoNei were incubated with 100 nM 4L substrate in the presence of 50 mM sodium borohydride. Completed reactions were mixed with an equal volume of 200 nM DAPI solution, incubated for 5 minutes at room temperature, and fluorescence was detected at 340 nm excitation/460 nm emission. Relative fluorescence (RF) readings to the 0 nM enzyme sample were used to determine the concentration of ES complex using the equation $ES=ST*(1-RF)$.
Figure 7:
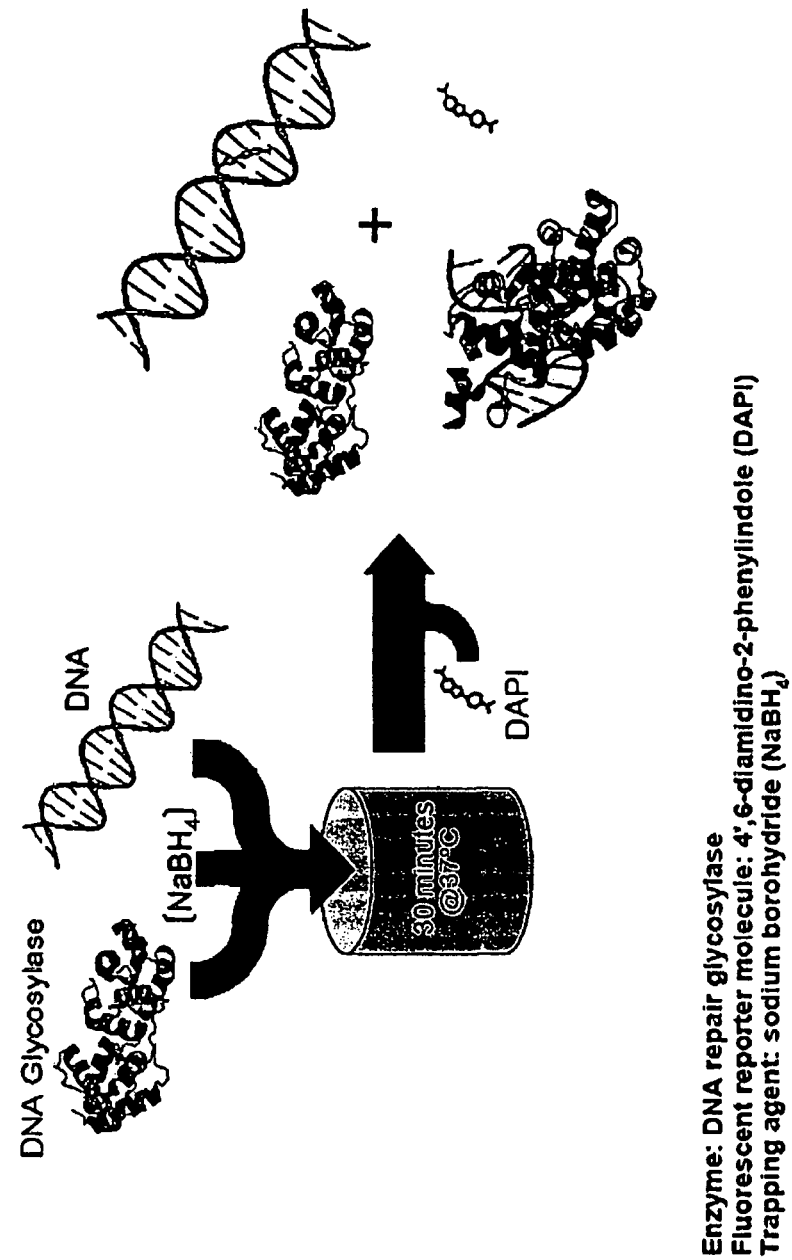
FIG. 7 is a schematic illustrating a certain embodiment of the molecular accessibility assay.
Figure 8:
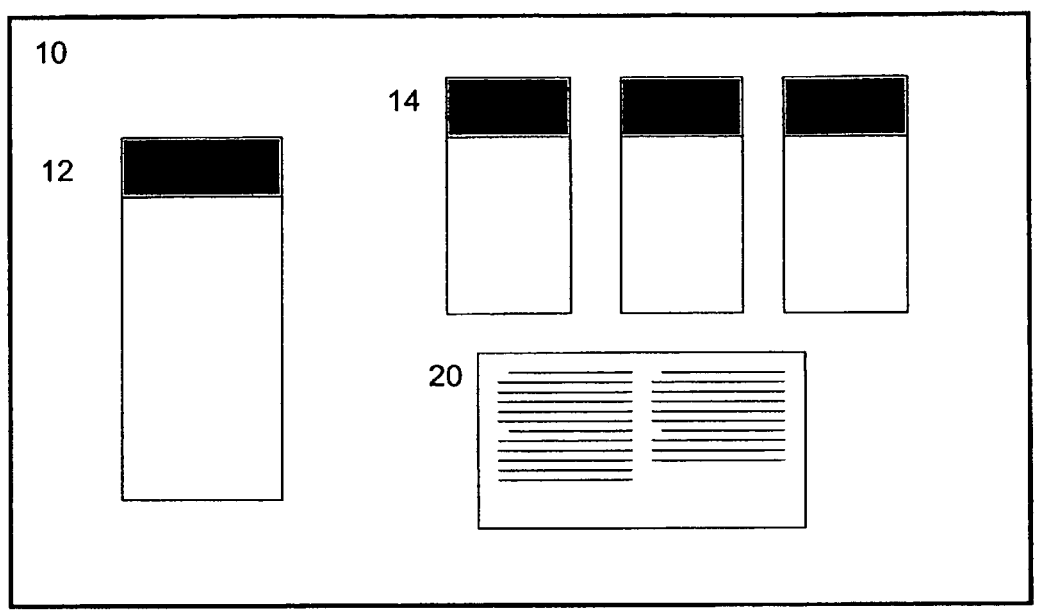
FIG. 8 is a schematic diagram of a kit for a molecular accessibility assay. (10=kit, 12=component for molecular accessibility assay; 14=additional components; 20=instructions).

To demonstrate the use of the accessibility assay with enzyme preparations having significantly different activities, two additional preparations were analyzed with the 4L substrate: an EcoNei purification known to have little activity and a more recent NEIL1 purification with good activity. Two concentrations were chosen for each, reflecting the prior knowledge of activity levels, and the desire to determine only the α values with a minimal amount of enzyme. FIG. 6 shows results from the assay, and gives further detail into the calculation of ES concentration based on relative fluorescence. The accessibility assay was able to accurately determine the α value for both the EcoNei preparation, with less than 5% activity, and the NEIL1 prep, with over 50% activity. Each of these was verified to be correct by traditional gel-based methods.

Discussion

This work demonstrates a novel approach to rapidly differentiate the number of bound vs. unbound enzymes to damaged oligonucleotides following Schiff base trapping. Though the assay described focused on determining the fraction of active molecules in enzyme preparations, the technique itself should be applicable to any study that necessitates quantifying the total number of trapped enzyme-DNA moieties.

Throughout this study a single damaged nucleotide, DHU, was used for all substrates. Although this is useful for comparisons made as a proof of concept, accurate determination of the active fraction of numerous enzymes can be performed with use of additional substrates. For example, for accurate determination of the active fraction of EcoFpg, 7,8-dihydro-8-oxoguanine (8-oxoG) may be used based on the greater affinity for that damage. Some damaged nucleotides, such as 5-formyluracil, may be less optimal in a substrate for use in the activity determination of certain enzymes, due to their low affinity for the damage (13). An optimal substrate for a given enzyme, based on prior knowledge, may be used for accurate activity calculations. For previously uncharacterized enzymes, analysis of numerous substrates may be performed. Strong reducing agents, such as $NaBH_4$, may not be optimal for use combination with damages that are extremely prone to reduction such as AP sites. In these cases $NaCNBH_3$, where the half-life of an AP site has been reported to be about 6 hours, may be used (22). Partial destruction of the substrate via reduction will not affect calculation of the α value, only the β value will be affected. With either the gel-based or DAPI-based methods, a strong reducing environment may possibly lead to inactivation of some enzyme molecules. Nonetheless, it is unlikely that both $NaBH_4$ and $NaCNBH_3$ will show the same rate of inactivation due to the inherent differences in their rate of reduction. A side-by-side test with both reducing agents (as was done in FIGS. 2 and 4) is arguably a valid control for demonstrating the lack of enzyme inactivation.

This study has demonstrated a rapid, fluorescence-based approach for determining the number of bound vs. unbound BER enzymes to damaged oligonucleotides following Schiff base trapping. The use of the 4L sequence context correctly determines enzyme activity from relative fluorescence calculations (no calibration necessary), for numerous DNA glycosylases from multiple phylogenetic families. The total experimental time was reduced from the standard 1-2 days using a traditional gel-based method, to under 1 hour for the DAPI-based method. In a 96-well microplate format the number of concurrent samples that can be tested also scales well. Additionally, neither radioactive nor fluorescent labels are required for substrate DNA. These benefits have allowed frequent activity monitoring of laboratory enzyme stocks. One enzyme that was tested was found to have dropped from over 80% activity to 20% within a matter of weeks after initial purification. The testing of numerous optimized storage conditions can now be accomplished in minimal time. The molecular accessibility assay should be useful in the study of numerous DNA binding proteins.

REFERENCES

1. Huffman, J. L., Sundheim, O. and Tainer, J. A. (2005) DNA base damage recognition and removal: new twists and grooves. *Mutat Res*, 577, 55-76.
2. Wallace, S. S. (2002) Biological consequences of free radical-damaged DNA bases. *Free Radic Biol Med*, 33, 1-14.
3. Berti, P. J. and McCann, J. A. (2006) Toward a detailed understanding of base excision repair enzymes: transition state and mechanistic analyses of N-glycoside hydrolysis and N-glycoside transfer. *Chem Rev*, 106, 506-555.
4. Stivers, J. T. and Jiang, Y. L. (2003) A mechanistic perspective on the chemistry of DNA repair glycosylases. *Chem Rev*, 103, 2729-2759.
5. Verdine, G. L. and Norman, D. P. (2003) Covalent trapping of protein-DNA complexes. *Annu Rev Biochem*, 72, 337-366.
6. Im, E. K., Hong, C. H., Back, J. H., Han, Y. S. and Chung, J. H. (2005) Functional identification of an 8-oxoguanine specific endonuclease from *Thermotoga maritima*. *J Biochem Mol Biol*, 38, 676-682.
7. Bandaru, V., Sunkara, S., Wallace, S. S. and Bond, J. P. (2002) A novel human DNA glycosylase that removes oxidative DNA damage and is homologous to *Escherichia coli* endonuclease VIII. *DNA Repair (Amst)*, 1, 517-529.
8. Dany, A. L. and Tissier, A. (2001) A functional OGG1 homologue from *Arabidopsis thaliana*. *Mol Genet Genomics*, 265, 293-301.
9. Ikeda, S., Biswas, T., Roy, R., Izumi, T., Boldogh, I., Kurosky, A., Sarker, A. H., Seki, S. and Mitra, S. (1998) Purification and characterization of human NTH1, a homolog of *Escherichia coli* endonuclease III. Direct identification of Lys-212 as the active nucleophilic residue. *J Biol Chem*, 273, 21585-21593.
10. Burgess, S., Jaruga, P., Dodson, M. L., Dizdaroglu, M. and Lloyd, R. S. (2002) Determination of active site residues in *Escherichia coli* endonuclease VIII. *J Biol Chem*, 277, 2938-2944.
11. Zharkov, D. O., Rosenquist, T. A., Gerchman, S. E. and Grollman, A. P. (2000) Substrate specificity and reaction mechanism of murine 8-oxoguanine-DNA glycosylase. *J Biol Chem*, 275, 28607-28617.
12. Marenstein, D. R., Ocampo, M. T., Chan, M. K., Altamirano, A., Basu, A. K., Boorstein, R. J., Cunningham, R. P. and Teebor, G. W. (2001) Stimulation of human endonuclease III by Y boxbinding protein I (DNA-binding protein B). Interaction between a base excision repair enzyme and a transcription factor. *J Biol Chem*, 276, 21242-21249.
13. Matsubara, M., Masaoka, A., Tanaka, T., Miyano, T., Kato, N., Terato, H., Ohyama, Y., Iwai, S. and Ide, H. (2003) Mammalian 5-formyluracil-DNA glycosylase. 1. Identification and characterization of a novel activity that releases 5-formyluracil from DNA. Biochemistry, 42, 4993-5002.
14. Doi, Y., Katafuchi, A., Fujiwara, Y., Hitomi, K., Tainer, J. A., Ide, H. and Iwai, S. (2006) Synthesis and characterization of oligonucleotides containing 2'-fluorinated thymidine glycol as inhibitors of the endonuclease III reaction. *Nucleic Acids Res,* 34, 1540-1551.
15. Back, J. H., Park, J. H., Chung, J. H., Kim, D. S. and Han, Y. S. (2006) A distinct TthMutY bifunctional glycosylase that hydrolyzes not only adenine but also thymine opposite 8-oxoguanine in the hyperthermophilic bacterium, *Thermus thermophilus. DNA Repair (Amst),* 5, 894-903.
16. Lu, A. L. and Wright, P. M. (2003) Characterization of an *Escherichia coli* mutant MutY with a cysteine to alanine mutation at the iron-sulfur cluster domain. *Biochemistry,* 42, 3742-3750.
17. Sidorkina, O. M. and Laval, J. (2000) Role of the N-terminal proline residue in the catalytic activities of the *Escherichia coli* Fpg protein. *J Biol Chem,* 275, 9924-9929.
18. Saparbaev, M., Sidorkina, O. M., Jurado, J., Privezentzev, C. V., Greenberg, M. M. and Laval, J. (2002) Repair of oxidized purines and damaged pyrimidines by *E. coli* Fpg protein: different roles of proline 2 and lysine 57 residues. *Environ Mol Mutagen,* 39, 10-17.
19. Zharkov, D. O., Gilboa, R., Yagil, I., Kycia, J. H., Gerchman, S. E., Shoham, G. and Grollman, A. P. (2000) Role for lysine 142 in the excision of adenine from A:G mispairs by MutY DNA glycosylase of *Escherichia coli. Biochemistry,* 39, 14768-14778.
20. Rieger, R. A., McTigue, M. M., Kycia, J. H., Gerchman, S. E., Grollman, A. P. and Iden, C. R (2000) Characterization of a cross-linked DNA-endonuclease VIII repair complex by electrospray ionization mass spectrometry. *J Am Soc Mass Spectrom,* 11, 505-515.
21. Zharkov, D. O., Rieger, R. A., Iden, C. R. and Grollman, A. P. (1997) NH2-terminal proline acts as a nucleophile in the glycosylase/AP-lyase reaction catalyzed by *Escherichia coli* formamidopyrimidine-DNA glycosylase (Fpg) protein. *J Biol Chem,* 272, 5335-5341.
22. Manuel, R. C., Hitomi, K., Arvai, A. S., House, P. G., Kurtz, A. J., Dodson, M. L., McCullough, A. K., Tainer, J. A. and Lloyd, R. S. (2004) Reaction intermediates in the catalytic mechanism of *Escherichia coli* MutY DNA glycosylase. *J Biol Chem,* 279, 46930-46939.
23. Kapuscinski, J. and Skoczylas, B. (1978) Fluorescent complexes of DNA with DAPI 4',6-diamidine-2-phenyl indole.2HCl or DCI 4',6-dicarboxyamide-2-phenyl indole. *Nucleic Acids Res,* 5, 3775-3799.
24. Manzini, G., Barcellona, M. L., Avitabile, M. and Quadrifoglio, F. (1983) Interaction of diamidino-2-phenylindole (DAPI) with natural and synthetic nucleic acids. *Nucleic Acids Res,* 11, 8861-8876.
25. Larsen, T. A., Goodsell, D. S., Cascio, D., Grzeskowiak, K. and Dickerson, R. E. (1989) The structure of DAPI bound to DNA. *J Biomol Struct Dyn,* 7, 477-491.
26. Vlieghe, D., Sponer, J. and Van Meervelt, L. (1999) Crystal structure of d(GGCCAATTGG) complexed with DAPI reveals novel binding mode. *Biochemistry,* 38, 16443-16451.
27. Trotta, E., D'Ambrosio, E., Del Grosso, N., Ravagnan, G., Cirilli, M. and Paci, M. (1993) $^1$H NMR study of [d(GC-GATCGC)]2 and its interaction with minor groove binding 4',6-diamidino-2-phenylindole. *J Biol Chem,* 268, 3944-3951.
28. Wilson, W. D., Tanious, F. A., Barton, H. J., Jones, R. L., Fox, K., Wydra, R. L. and Strekowski, L. (1990) DNA sequence dependent binding modes of 4',6-diamidino-2-phenylindole (DAPI). *Biochemistry,* 29, 8452-8461.
29. Mohan, S. and Yathindra, N. (1994) A study of the interaction of DAPI with DNA containing AT and non-AT sequences—molecular specificity of minor groove binding drugs. *J Biomol Struct Dyn,* 11, 849-867.
30. Albert, F. G., Eckdahl, T. T., Fitzgerald, D. J. and Anderson, J. N. (1999) Heterogeneity in the actions of drugs that bind in the DNA minor groove. *Biochemistry,* 38, 10135-10146.
31. Eriksson, S., Kim, S. K., Kubista, M. and Norden, B. (1993) Binding of 4',6-diamidino-2-phenylindole (DAPI) to AT regions of DNA: evidence for an allosteric conformational change. *Biochemistry,* 32, 2987-2998.
32. Zaitsev, E. N. and Kowalczykowski, S. C. (1998) Binding of double-stranded DNA by *Escherichia coli* RecA protein monitored by a fluorescent dye displacement assay. *Nucleic Acids Res,* 26, 650-654.
33. Eggleston, A. K., Rahim, N. A. and Kowalczykowski, S. C. (1996) A helicase assay based on the displacement of fluorescent, nucleic acid-binding ligands. *Nucleic Acids Res,* 24, 1179-1186.
34. Bandaru, V., Blaisdell, J. O. and Wallace, S. S. (2006) Oxidative DNA glycosylases: recipes from cloning to characterization. *Methods Enzymol,* 408, 15-33.
35. Spackova, N., Cheatham, T. E., 3rd, Ryjacek, F., Lankas, F., Van Meervelt, L., Hobza, P. and Sponer, J. (2003) Molecular dynamics simulations and thermodynamics analysis of DNA-drug complexes. Minor groove binding between 4',6-diamidino-2-phenylindole and DNA duplexes in solution. *J Am Chem Soc,* 125, 1759-1769.
36. Fromme, J. C. and Verdine, G. L. (2003) Structure of a trapped endonuclease III-DNA covalent intermediate. *Embo J,* 22, 3461-3471.
37. Gilboa, R., Zharkov, D. O., Golan, G., Fernandes, A. S., Gerchman, S. E., Matz, E., Kycia, J. H., Grollman, A. P. and Shoham, G. (2002) Structure of formamidopyrimidine-DNA glycosylase covalently complexed to DNA. *J Biol Chem,* 277, 19811-19816.
38. Holub, O. and Clegg, R. M. (1999), *The 43rd Annual Meeting of the Biophysical Society.* Biophysical Journal (Annual Meeting Abstracts), Baltimore, Md., Vol. 76, pp. A129.
39. Porello, S. L., Leyes, A. E. and David, S. S. (1998) Single-turnover and pre-steady-state kinetics of the reaction of the adenine glycosylase MutY with mismatch-containing DNA substrates. *Biochemistry,* 37, 14756-14764.
40. Williams, S. D. and David, S. S. (1998) Evidence that MutY is a monofunctional glycosylase capable of forming a covalent Schiff base intermediate with substrate DNA. *Nucleic Acids Res,* 26, 5123-5133.
41. Williams, S. D. and David, S. S. (1999) Formation of a Schiff base intermediate is not required for the adenine glycosylase activity of *Escherichia coli* MutY. *Biochemistry,* 38, 15417-15424.
42. Hashimoto, M., Greenberg, M. M., Kow, Y. W., Hwang, J. T. and Cunningham, R. P. (2001) The 2-deoxyribonolactone lesion produced in DNA by neocarzinostatin and other damaging agents forms cross-links with the base-excision repair enzyme endonuclease III. *J Am Chem Soc,* 123, 3161-3162.
43. DeMott, M. S., Beyret, E., Wong, D., Bales, B. C., Hwang, J. T., Greenberg, M. M. and Demple, B. (2002) Covalent trapping of human DNA polymerase beta by the oxidative DNA lesion 2-deoxyribonolactone. *J Biol Chem,* 277, 7637-7640.
44. Nakano, T., Terato, H., Asagoshi, K., Masaoka, A., Mukuta, M., Ohyama, Y., Suzuki, T., Makino, K. and Ide, H. (2003) DNA-protein cross-link formation mediated by oxanine. A novel genotoxic mechanism of nitric oxide-induced DNA damage. *J Biol Chem,* 278, 25264-25272.

45. Ide, H. and Kotera, M. (2004) Human DNA glycosylases involved in the repair of oxidatively damaged DNA. *Biol Pharm Bull*, 27, 480-485.
46. Travers, A. A. (1989) DNA conformation and protein binding. *Annu Rev Biochem*, 58, 427-452.
47. Neidle, S. (1992) Minor-groove width and accessibility in B-DNA drug and protein complexes. *FEBS Lett*, 298, 97-99.
48. Chuprina, V. P., Heinemann, U., Nurislamov, A. A., Zielenkiewicz, P., Dickerson, R. E. and Saenger, W. (1991) Molecular dynamics simulation of the hydration shell of a B-DNA decamer reveals two main types of minor-groove hydration depending on groove width. *Proc Natl Acad Sci USA*, 88, 593-597.
49. Ghosh, A. and Bansal, M. (1999) C—H.O hydrogen bonds in minor groove of A-tracts in DNA double helices. *J Mol Biol*, 294, 1149-1158.
50. Van Hecke, K., Nam, P. C., Nguyen, M. T. and Van Meervelt, L. (2005) Netropsin interactions in the minor groove of d(GGCCAATTGG) studied by a combination of resolution enhancement and ab initio calculations. *Febs J*, 272, 3531-3541.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

I claim:

1. A method for assaying the amount of bound nucleic acid-binding polypeptide in a sample comprising the steps of:
    (a) measuring the level of fluorescence in a sample comprising a nucleic acid, a nucleic acid-binding fluorescent reporter, and a nucleic acid-binding polypeptide, wherein the nucleic acid comprises a fluorescent reporter-binding sequence and a binding polypeptide-binding sequence positioned such that binding polypeptide bound to the nucleic acid inhibits binding of the fluorescent reporter to the nucleic acid and modulates the level of fluorescence in the sample, and wherein the binding-polypeptide binding sequence of the nucleic acid is one or more damaged nucleic acid bases, and wherein the fluorescent reporter is fluorescent 4',6-diamidino-2-phenylindole (DAPI), distamycin A, Hoechst 33258, netropsin, berenil, 2-hydroxystilbamidine, chromomycin A3, or a fluorophore-tethered peptide or oligopeptide, and
    (b) comparing the level of fluorescence in the sample to a control level of fluorescence, wherein a difference in the level of fluorescence in the sample compared to the control level of fluorescence indicates the amount of bound nucleic acid-binding polypeptide in the sample.

2. The method of claim 1, wherein the nucleic acid-binding polypeptide is a DNA-binding polypeptide.

3. The method of claim 2, wherein the DNA-binding polypeptide is an enzyme, histone, telomere binding polypeptide, transcription factor, or other regulatory polypeptide.

4. The method of claim 3, wherein the enzyme is a glycosylase, polymerase, nuclease, methyl transferase, or topoisomerase.

5. The method of claim 1, wherein the sample is obtained from an enzyme preparation or cell extract.

6. The method of claim 1, wherein the fluorescent reporter is a fluorescent molecule whose fluorescence is modified when the reporter binds a nucleic acid compared to the fluorescence of the reporter when not bound to the nucleic acid.

7. The method of claim 1, wherein the nucleic acid has a sequence comprising two or more fluorescent reporter-binding sequences and/or two or more binding-polypeptide binding sequences positioned such that binding polypeptide bound to the nucleic acid interferes with binding of the fluorescent reporter to the nucleic acid.

8. The method of claim 1, wherein the nucleic acid is a natural, synthetic, or modified DNA or RNA.

9. The method of claim 1, wherein the damaged nucleic acid bases comprise at least one 5,6-dihydrouracil, 7,8-dihydro-8-oxoguanine, 5,6-dihydroxy-5,6-dihydrothymine, 5-hydroxycytosine, 5,6-dihydrothymine, 5-hydroxyuracil, or 7,8-dihydro-8-oxoadenine.

10. The method of claim 1, wherein the binding polypeptide is covalently or non-covalently bound to the nucleic acid.

11. The method of claim 10, wherein the binding polypeptide is covalently bound to the nucleic acid by an intermediate trapped by a trapping agent.

12. The method of claim 11, wherein the intermediate is a Schiff base.

13. The method of claim 11, wherein the trapping agent is 2-deoxyribonolactone, oxanine, or, cis-Platinum.

14. The method of claim 11, wherein the trapping agent is a reducing agent.

15. The method of claim 14, wherein the reducing agent is a borohydride compound, $NaBH_4$ or $NaCNBH_3$.

* * * * *

UNITED STATES PATENT AND TRADEMARK OFFICE
CERTIFICATE OF CORRECTION

PATENT NO. : 8,546,083 B2  
APPLICATION NO. : 12/449042  
DATED : October 1, 2013  
INVENTOR(S) : Jeffrey O. Blaisdell Page 1 of 1

It is certified that error appears in the above-identified patent and that said Letters Patent is hereby corrected as shown below:

On the Title Page, Item (73) please amend the Assignees section to read:

"The University of Vermont and State Agricultural College, Burlington, VT (US)"

Signed and Sealed this
Twenty-second Day of April, 2014

Michelle K. Lee
*Deputy Director of the United States Patent and Trademark Office*

SEQUENCE LISTING

```
<160> NUMBER OF SEQ ID NOS: 5

<210> SEQ ID NO 1
<211> LENGTH: 35
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (14)..(14)
<223> OTHER INFORMATION: n is 5,6-dihydrouracil

<400> SEQUENCE: 1
tgtcaatagc aagnggagaa gtcaatcgtg agtct                             35

<210> SEQ ID NO 2
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (13)..(13)
<223> OTHER INFORMATION: n is 5,6-dihydrouracil or cytosine

<400> SEQUENCE: 2
gccccgccaa ttnccgccgc cgcc                                         24

<210> SEQ ID NO 3
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (14)..(14)
<223> OTHER INFORMATION: n is 5,6-dihydrouracil or cytosine

<400> SEQUENCE: 3
gccccgccaa ttcnccgccg ccgcc                                        25

<210> SEQ ID NO 4
<211> LENGTH: 32
<212> TYPE: DNA
<213> ORGANISM: Artificial Sequence
<220> FEATURE:
```

```
<223> OTHER INFORMATION: Synthetic Oligonucleotide
<220> FEATURE:
<221> NAME/KEY: misc_feature
<222> LOCATION: (17)..(17)
<223> OTHER INFORMATION: n is 5,6-dihydrouracil or cytosine

<400> SEQUENCE: 4
gccccgccgc cccgccnaat tccgccgccg cc                                      32

<210> SEQ ID NO 5
<211> LENGTH: 33
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (17)..(17)
<223> OTHER INFORMATION: n is 5,6-dihydrouracil or cytosine

<400> SEQUENCE: 5
gccccgccgc cccgccncaa ttccgccgcc gcc                                     33
```